United States Patent
Larsen et al.

(10) Patent No.: US 10,787,653 B2
(45) Date of Patent: Sep. 29, 2020

(54) MARINE DNA POLYMERASES

(71) Applicant: Universitetet I Tromsø—Norges Arktiske Universitet, Tromsø (NO)

(72) Inventors: Atle Noralf Larsen, Tromsø (NO); Yvonne Piotrowski, Tromsø (NO); Netsanet Gizaw Assefa, Tromsø (NO); Olav Lanes, Tromsø (NO)

(73) Assignee: UNIVERSITETET I TROMSØ—NORGES ARKTISKE UNIVERSITET, Tromsø (NO)

( * ) Notice: Subject to any disclaimer, the term of this patent is extended or adjusted under 35 U.S.C. 154(b) by 0 days.

(21) Appl. No.: 16/087,242

(22) PCT Filed: Mar. 22, 2017

(86) PCT No.: PCT/EP2017/056865
§ 371 (c)(1),
(2) Date: Sep. 21, 2018

(87) PCT Pub. No.: WO2017/162765
PCT Pub. Date: Sep. 28, 2017

(65) Prior Publication Data
US 2019/0106686 A1    Apr. 11, 2019

(30) Foreign Application Priority Data
Mar. 22, 2016    (GB) .................................. 1604876.1

(51) Int. Cl.
*C12N 9/12*    (2006.01)
*C12Q 1/6844*    (2018.01)

(52) U.S. Cl.
CPC ......... *C12N 9/1252* (2013.01); *C12Q 1/6844* (2013.01); *C12Q 2521/101* (2013.01);
(Continued)

(58) Field of Classification Search
None
See application file for complete search history.

(56) References Cited

U.S. PATENT DOCUMENTS

| 8,993,298 B1 | 3/2015 | Ong et al. | |
| 2005/0037412 A1* | 2/2005 | Meier | C12N 9/1252 435/6.11 |
| 2019/0106686 A1* | 4/2019 | Larsen | C12Q 1/6844 |

OTHER PUBLICATIONS

UniProt Accession No. A0A0M3RBD1_9BACI, published Dec. 9, 2015 (Year: 2015).*

(Continued)

*Primary Examiner* — Richard C Ekstrom
(74) *Attorney, Agent, or Firm* — Rothwell, Figg, Ernst & Manbeck, P.C.

(57) ABSTRACT

The present invention relates to DNA polymerases. In particular, the present invention relates to DNA polymerases based on a DNA polymerase from a *Psychrobacillus* sp. The present invention provides an isolated DNA polymerase or an enzymatically active fragment thereof, said DNA polymerase comprising the amino acid sequence of SEQ ID NO:1 or comprising an amino acid sequence which is at least 70% identical to SEQ ID NO:1. The invention also provides nucleic acid molecules comprising a nucleotide sequence that encodes the DNA polymerase. The invention also provides a method of nucleotide polymerisation and a method of amplifying a nucleic acid in which the DNA polymerase or an enzymatically active fragment thereof is used.

22 Claims, 8 Drawing Sheets

Specification includes a Sequence Listing.

(52) U.S. Cl.
CPC .. *C12Q 2531/101* (2013.01); *C12Q 2531/119* (2013.01); *C12Q 2531/125* (2013.01); *C12Y 207/07007* (2013.01)

(56) References Cited

OTHER PUBLICATIONS

International Search Report and Written Opinion issued in PCT/EP2017/056865 dated Jun. 7, 2017 (14 pages).
Database Uniprot [Online] Dec. 9, 2015, "RecName: Full=DNA polymerase {ECO:0000256, RuleBase: RU004460};" Database accession No. A0A0M3RBD1 XP002769996 (2 pages).
Database Uniprot [Online] Jan. 20, 2016, "RecName: Full=DNA polymerase {ECO:0000256, RuleBase: RU004460};" Database accession No. A0A0Q3VXV0 XP002769997 (2 pages).
Bei, Han et al. "Preliminary characterization of a thermostable DNA polymerase I from a mesophilic Bacillus sphaericus strain C3-41" Archives of Microbiology, Springer, Berlin, DE, vol. 186, No. 3, Jul. 12, 2006, pp. 203-209, XP019419707 (7 pages).
Database GenBank [Online] NCBI: "*Bacillus* sp. FJAT-22090 genome" Database accession No. CP012601, Sep. 4, 2015, XP002769998 (4 pages).
Anonymous: "Which DNA polymerase is best for my isothermal amplification reaction?, NEB", Jan. 1, 2013, Retrieved from the Internet, XP055370765 (1 page).
New England Biolabs: "Bsu DNA Polymerase Selection Chart, NEB", Mar. 19, 2016, Retrieved from the Internet, XP055370813 (3 pages).
New England Biolabs: "Bsu DNA Polymerase, Large Fragment, NEB", Sep. 19, 2015, Retrieved from the Internet, XP055370889 (2 pages).
Database Uniprot [Online] Dec. 15, 1998, "RecName: Full=DNA polymerase I; Short=POL I; EC=2.7.7.7;", Database accession No. 034996 XP002769999 (2 pages).
Anonymous: "IsoPol (TM) DNA Polymerase", Dec. 1, 2016, Retrieved from the Internet, XP055370899 (2 pages).
Feller, G. "Molecular adaptations to cold in psychrophilic enzymes" CMLS Cellular and molecular Life Sciences, Basel, CH, 60 (2003), pp. 648-662 (15 pages).
Krishnamurthi, S. "*Psychrobacillus* gen. nov. and proposal for reclassification of Bacillus insolitus Larkin & Stokes, 1967, B psychrotolerans Abd-El Rahman et al., 2002 and B. psychrodurans Abd-El Rahman et al., 2002 as *Psychrobacillus insolitus* comb. nov., *Psychrobacillus psychrotolerans* comb. nov. and *Psychrobacillus psychrodurans* comb. nov.", Systematic and Applied Microbiology 33 (2010), pp. 367-373 (7 pages).
Rozanov, Aleksey S. et al. "Draft Genome Sequences of Geobacillus stearothermophilus Strains 22 and 53, Isolated from the Garga Hot Spring in the Barguzin River Valley of the Russian Federation" Genome Announcements, vol. 2, No. 6, Nov./Dec. 2014, (2 pages).
Gill, P. and A. Ghaemi (2008) :"Nucleic Acid Isothermal Amplification Technologies—A Review", Nucleosides Nucleotides Nucleic Acids 27(3): 224-243.
Craw, P. and W. Balachandran (2012) :"Isothermal nucleic acid amplification technologies for point-of-care diagnostics: a critical review", Lab Chip 12(14): 2469-2486.
De Paz, H. D. et al. (2014) :"Molecular isothermal techniques for combating infectious diseases: towards low-cost poin-of-care diagnostics", Expert Rev Mol Diagn 14(7): 1-17.
Yan, L. et al. (2014) :"Isothermal amplified detection of DNA and RNA", Mol Biosyst 10(5): 970-1003).
Ma et al.: "Isothermal amplification method for next-generation sequencing", 2013, Proc Natl Acad Sci U S A 110(35): 14320-14323.

\* cited by examiner

MARINE DNA POLYMERASES

CROSS-REFERENCE TO RELATED APPLICATIONS

The present application is a national stage filing under 35 U.S.C. §371 of PCT/EP2017/056865, filed on 22 Mar. 2017, which in turn claims the benefit of priority to and the benefit of GB Application No. 1604876.1, filed 22 Mar. 2016. Each application is incorporated herein by reference in its entirety.

The present invention relates to DNA polymerases. In particular, the present invention relates to DNA polymerases based on a DNA polymerase from a *Psychrobacillus* sp.

The gold standard of microbial identification still remains culturing and subsequent phenotypic differentiation of the causative agent, a process often taking several days to perform and analyze, and this delay may have major impact on morbidity and mortality of an infectious disease. In addition, many organisms cannot grow on culture media, hence, will be undetected by existing culturing methods. The Polymerase Chain Reaction (PCR) in many ways revolutionized the molecular genetics and diagnosis field. The workhorses in PCR technology, are thermostable high fidelity DNA polymerases which together with cyclic events of heating and cooling to obtain strand separation, primer annealing and elongation, lead to amplification of a target DNA sequence. PCR technology is now widely employed in biomedical and life science research as well as molecular diagnostics.

Point-of-care (POC) diagnostics are described as medical tools or devices enabling disease diagnosis in a patient's community outside a hospital setting. The ideal diagnostic test should meet the "ASSURED" criteria: Affordable, Sensitive, Specific, User-friendly, Rapid and robust, Equipment-free and Delivered to those who need it. Although PCR technology has a high potential, it still has limitations and requires the use of high precision electrically powered thermal cycling equipment for repeated heating and cooling processes and skilled personnel to run the equipment. Non-specific amplification due to spurious priming in the annealing process is problematic, and PCR is also prone to inhibitory compounds in "crude" samples. In addition, the bulky design of PCR devices make PCR an imperfect solution for incorporation into POC technology platforms and make PCR-based methods difficult to employ as the major technology driver in POC diagnostics.

Lately, an increased focus on non-PCR based methods, or Isothermal Amplification methods, has emerged. In these methods, nucleic acid amplification takes place at constant (moderate) temperatures and has no need for high precision temperature cycling and control, or enzymes stable at high temperatures. Isothermal amplification methods are reported to have analytical sensitivities and specificities comparable to PCR as well as a higher tolerance to inhibitory compounds, while allowing shorter time to results and easier use. These features make isothermal amplification methods highly desirable for those developing POC molecular diagnostics platforms and aiming to meet "ASSURED" criteria. A number of methods have in the last decade been published for isothermal amplification of nucleic acids (both RNA and DNA) (Reviewed by Gill, P. and A. Ghaemi (2008) *Nucleosides Nucleotides Nucleic Acids* 27(3): 224-243; Craw, P. and W. Balachandran (2012) *Lab Chip* 12(14): 2469-2486; de Paz, H. D. et al. (2014) *Expert Rev Mol Diagn* 14(7): 827-843; Yan, L. et al. (2014) *Mol Biosyst* 10(5): 970-1003). In several of the methods, success relies on the inherent strand displacement activity of the DNA polymerase used in the reaction setup. The term strand displacement describes the ability of the polymerase to displace downstream DNA encountered during synthesis.

In addition to diagnostics also other areas of interest benefit from isothermal amplification technology empowered by the DNA polymerase. In this regard, whole genome amplification (multiple displacement amplification) is important for genomic research especially when limited amount of DNA is present and/or in single cell approaches. Also in next-generation sequencing approaches, either commercially available or at the proof of concept stage, strand-displacing polymerases are important as exemplified by the Pacific Biosciences Single Molecule Real Time (SMRT) DNA sequencing technology and an isothermal amplification method for next generation sequencing published in 2013 by Ma et al. (Ma, Z. et al. *Proc Natl Acad Sci USA* 110(35): 14320-14323).

The current toolbox of polymerase enzymes used in the various isothermal technologies is, however, very limited. Typically, different isothermal methods require reaction temperatures between 30-65° C. which are mainly determined by the working range of the polymerases used in the reactions.

The *E. coli* Klenow fragment DNA polymerase, for example, exhibits useful levels of polymerase activity in only a relatively narrow temperatures range and has relatively low activity at low-to-moderate temperatures (e.g. at 25° C.). What are needed in the art are DNA polymerases which exhibit useful levels of polymerase activity and good stability at a broad range of temperatures, in particular at low-to-moderate temperatures, but preferably also at higher temperatures. Such polymerases would be useful for isothermal amplification reactions performed at a broad range of temperatures, including temperatures at or close to room temperature. The inventors have identified a DNA polymerase from a *Psychrobacillus* sp. which surprisingly fulfils these criteria. The *Psychrobacillus* sp. is cold adapted and its DNA polymerase I is active at low temperatures. However, unlike other marine DNA polymerases, the *Psychrobacillus* sp. DNA polymerase I is not rapidly inactivated above 20-25° C. and thus represents a DNA polymerase that is very useful at a broad range of temperatures. Moreover, the *Psychrobacillus* sp. DNA polymerase I is much more active in general than other marine polymerases.

Therefore, in a first aspect the invention provides an isolated DNA polymerase or an enzymatically active fragment thereof, said DNA polymerase comprising the amino acid sequence of SEQ ID NO:1 or comprising an amino acid sequence which is at least 70% identical to SEQ ID NO:1.

The DNA polymerase of SEQ ID NO:1 is based on the amino acid sequence of DNA polymerase I from a *Psychrobacillus* species (also referred to herein as PB or Pb or Pbl), a marine bacteria isolated in North of Norway. However, SEQ ID NO:1 lacks the 5'-3'-exonuclease domain that is present in the wild-type *Psychrobacillus* species DNA polymerase I sequence. In preferred embodiments, the 5'-3'-exonuclease domain is absent from the DNA polymerase enzyme as 5'-3'-exonuclease activity is typically unwanted as it may degrade primers and/or products in an amplification mixture.

In some embodiments, the invention provides an isolated DNA polymerase or an enzymatically active fragment thereof, said DNA polymerase consisting of the amino acid sequence of SEQ ID NO:1 or consisting of an amino acid sequence which is at least 70% identical to SEQ ID NO:1.

In preferred embodiments, the DNA polymerase of the invention comprises (or consists of) an amino acid sequence that is at least 71%, at least 72%, at least 73%, at least 74%, at least 75%, preferably at least 80%, 85%, 90% or 95%, e.g. at least 98% or 99% or 99.5%, identical to SEQ ID NO:1.

In some embodiments, the DNA polymerase of the invention comprises (or consists of) an amino acid sequence that has single or multiple amino acid alterations (additions, substitutions, insertions or deletions) compared to SEQ ID NO:1. Such sequences preferably may contain up to 5, e.g. only 1, 2, 3, 4 or 5, preferably 1, 2 or 3, more preferably 1 or 2, altered amino acids. Substitutions can be with conservative or non-conservative amino acids. Preferably said alterations are conservative amino acid substitutions.

Preferably, the DNA polymerase of the invention comprises the amino acid sequence of SEQ ID NO:1.

In a preferred embodiment, the DNA polymerase consists of the amino acid sequence of SEQ ID NO:1.

In one embodiment, the DNA polymerase comprises (or consists of) the amino acid sequence of SEQ ID NO:3. The present invention also provides variants and fragments of SEQ ID NO:3. The types of variants and fragments of SEQ ID NO:1 described herein apply, mutatis mutandis, to variants and fragments of SEQ ID NO:3.

Enzymatically active fragments of DNA polymerases of the invention are also provided. Enzymatically active fragments are fragments that have DNA polymerase activity. Enzymatically active fragments may be at least 400, at least 450, at least 475, at least 500, at least 525, at least 550, at least 560, at least 570 or at least 575 amino acids in length. Preferred fragments are at least 525, at least 550, at least 560, at least 570 or at least 575 amino acids in length. The fragments are at least 70%, preferably at least 80%, at least 85% or at least 90%, more preferably at least 95% (e.g. at least 98% or 99% or 99.5%), or 100% identical to the corresponding portion of SEQ ID NO:1.

For any given DNA polymerase there is generally a temperature at which maximum polymerase activity is observed. For many DNA polymerases, when the temperature deviates (e.g. decreases or increases) from the temperature at which maximum activity is observed, there is generally a marked decrease in polymerase activity, even at only modest temperature deviations, meaning that many polymerases are only suitable for use in applications carried out in a fairly narrow temperature range.

The present inventors have found that, advantageously, at a broad range of temperatures, including at low to modest temperatures, DNA polymerase I of a *Psychrobacillus* species exhibits substantial DNA polymerase activity relative to the DNA polymerase activity at the temperature at which maximum polymerase activity is observed. Put another way, the inventors have found that unlike many DNA polymerases, the DNA polymerase I of this *Psychrobacillus* species exhibits a useful proportion of its maximum polymerase activity at temperatures which differ significantly from the temperature at which the maximum activity is observed.

Accordingly, in some embodiments DNA polymerases of the present invention exhibit across a broad range of temperatures a substantial proportion of their maximum polymerase activity.

In preferred embodiments, the temperature at which the DNA polymerase exhibits its maximum activity is about 37° C. to 42° C., preferably 37° C.–40° C. (e.g. 37, 38, 39 or 40° C.).

Some DNA polymerases of the present invention exhibit a substantial proportion of their maximum polymerase activity across the temperature range from 0° C. to 35° C.

Some DNA polymerases of the present invention exhibit at least 30% of their maximum polymerase activity across the temperature range from 0° C. to 35° C.

Some DNA polymerases of the present invention exhibit at least 40% of their maximum polymerase activity across the temperature range from 10° C. to 35° C.

Some DNA polymerases of the present invention exhibit at least 50% of their maximum polymerase activity across the temperature range from 15° C. to 35° C.

Some DNA polymerases of the present invention exhibit at least 60% of their maximum polymerase activity across the temperature range from 20° C. to 35° C.

Some DNA polymerases of the present invention exhibit at least 70% (preferably at least 80% or at least 90%) of their maximum polymerase activity across the temperature range from 30° C. to 35° C.

In some embodiments, at a temperature that deviates (increase or decrease) by up to about 10° C. (e.g. 1, 2, 3, 4, 5, 6, 7, 9, or 10° C.) from the temperature at which the polymerase exhibits maximum activity, DNA polymerases of the present invention exhibit at least about 30% of their maximum polymerase activity.

In some embodiments, at a temperature that deviates (increase or decrease) by up to about 5° C. (e.g. 1, 2, 3, 4, 5° C.) from the temperature at which the polymerase exhibits maximum activity, DNA polymerases of the present invention exhibit at least about 60% of their maximum polymerase activity.

In some embodiments, at a temperature that is up to about 35° C. to 40° C. lower (e.g. 40° C., 30° C., 20° C., 10° C., or 5° C. lower) than the temperature at which the polymerase exhibits maximum activity, DNA polymerases of the present invention exhibit at least about 30% of their maximum polymerase activity.

In some embodiments, at a temperature that is up to about 12° C. to about 15° C. lower (e.g. 1, 2, 3, 4, 5, 10, 12 or 15° C. lower) than the temperature at which the polymerase exhibits maximum activity, DNA polymerases of the present invention exhibit at least about 60% of their maximum polymerase activity.

In some embodiments, at a temperature that is up to about 5° C. to about 10° C. lower (e.g. 1, 2, 3, 4, 5, 6, 7, 8, 9 or 10° C. lower) than the temperature at which the polymerase exhibits maximum activity, DNA polymerases of the present invention exhibit at least about 70% of their maximum polymerase activity (preferably at least about 70%, 75%, 80%, 85%, 90% or 95% of their maximum polymerase activity).

Suitable assays for analysing DNA polymerase activity are known in the art. Such assays can thus be used to determine DNA polymerase activity at any given temperature relative to the DNA polymerase activity that is exhibited at the temperature at which the polymerase exhibits its maximum activity. DNA polymerase activity as discussed above may be assessed using a single-nucleotide incorporation assay. In an exemplary single-nucleotide incorporation assay, a primer consisting of 19 nucleotides, which is labelled with a fluorophore at its 5' end, is annealed to a template DNA strand consisting of 40 nucleotides; in the reaction set up the only dNTP present is dATP thus the polymerase can extend the primer in the 5'-3' direction only by one nucleotide at position 20 (as there is one T at the corresponding (complementary) position on the template strand); subsequent analysis on a denaturing polyacrylamide gel (e.g. 12% polyacrylamide/7M urea) and scanning for the fluorophore labeled oligonucleotides shows the primer consisting of 19 oligonucleotides and the primer extended by the nucleotide adenine thus consisting of 20 oligonucleotides; enzyme activity (i.e. polymerase activity) is determined by densitometric measurement of bands representing the extended primer (intensity 1) and the unextended primer (intensity 0); the relative incorporation rate is calculated as follows: incorporation [%]=intensity 1/(intensity 0+intensity 1)*100.

Thus, DNA polymerase activity may be assessed in an assay having the steps of (i) providing a primer consisting of 19 nucleotides, which is labelled with a fluorophore at its 5' end, (ii) annealing said primer to a template DNA strand consisting of 40 nucleotides to form a primer-template complex, (iii) incubating said annealed primer-template complex with a DNA polymerase at the relevant temperature (i.e. temperature under investigation) in the presence of the only dNTP that is to be incorporated into the primer at position 20 at the 3' end of the primer (said dNTP is complementary to the relevant nucleotide on the annealed template DNA strand) and (iv) determining the amount of extended primer (20 nucleotides) compared with unextended primer (19 nucleotides) wherein the amount of extended primer relative to unextended primer corresponds to the level of polymerase activity (i.e. higher amounts of extended primer indicate higher polymerase activity).

Preferred primer and template strands are as described in the Example.

A particularly preferred single-nucleotide incorporation assay is described in the Example section herein. Thus, in preferred embodiments, relative DNA polymerase activities are as assessed in accordance with the single-nucleotide incorporation assay described in the Example section.

The present inventors have also surprisingly found that at a broad range of temperatures, including at temperatures significantly higher than its normal marine environment, the DNA polymerase I of this *Psychrobacillus* species shows good stability (temperature stability) in comparison with many other DNA polymerases, in particular in comparison with DNA polymerases from other marine organisms such as *Aliivibrio Salmonicida*. In this context, a "stable" DNA polymerase means that the DNA polymerase does not exhibit a substantial loss of polymerase activity after exposure to a broad range of temperatures. Alternatively viewed, good "stability" means that a DNA polymerase retains substantial polymerase activity (i.e. has substantial residual activity) after exposure to a broad range of temperatures.

Accordingly, some DNA polymerases of the present invention retain a substantial proportion of their maximum polymerase activity after incubation (pre-incubation) at a broad range of temperatures prior to assessing the DNA polymerase activity. In this context, the maximum polymerase activity may be the polymerase activity observed when the incubation (pre-incubation) of the DNA polymerase is done on ice (about 0° C.) prior to the initiation of the DNA polymerase activity assay.

Preferably, the incubation (pre-incubation) is for about 15 minutes (15 minutes is preferred). Preferably, irrespective of the temperature of the incubation (pre-incubation), the DNA polymerase is cooled on ice after said incubation (e.g. for about 5 minutes) prior to assessing DNA polymerase activity.

Some DNA polymerases of the present invention exhibit at least 40% of their maximum activity after incubation of the DNA polymerase at any temperature across the temperature range from 0° C. to 40° C. (e.g. from 0° C. to 15° C., 0° C. to 20° C., or 0° C. to 25° C., or 0° C. to 37° C.) prior to assessing DNA polymerase activity. Preferably, the DNA polymerase activity is as assessed at about 25° C. (25° C. is preferred).

Some DNA polymerases of the present invention exhibit at least 60% (preferably at least 70% or at least 80%) of their maximum activity after incubation of the DNA polymerase at any temperature across the temperature range from 0° C. to 37° C. (e.g. from 0° C. to 15° C., 0° C. to 20° C., or 0° C. to 25° C., 0° C. to 30° C., or 0° C. to 35° C.) prior assessing DNA polymerase activity. Preferably, the DNA polymerase activity is as assessed at about 25° C. (25° C. is preferred).

Some DNA polymerases of the present invention exhibit at least 70% (preferably at least 80%, at least 90%, at least 95% or 100%) of their maximum activity after incubation of the DNA polymerase at any temperature across the temperature range from 0° C. to 30° C. (e.g. from 0° C. to 15° C., 0° C. to 20° C., or 0° C. to 25° C.) prior to assessing DNA polymerase activity assay. Preferably, the DNA polymerase activity is as assessed at about 25° C. (25° C. is preferred).

In some embodiments, after a 15 minute incubation at 37° C. prior to the initiation of a DNA polymerase activity assay (e.g. a single-nucleotide extension reaction), DNA polymerases of the present invention exhibit at least 60% (preferably at least 70%, more preferably at least 80%) of the polymerase activity observed when the 15 minute incubation prior to the initiation of the DNA polymerase activity assay was done on ice (0° C.), i.e. there is at least 60%, at least 70% or at least 80% "residual" activity.

In some embodiments, after a 15 minute incubation at 30° C. prior to the initiation of a DNA polymerase activity assay (e.g. a single-nucleotide extension reaction), DNA polymerases of the present invention exhibit least 70% (preferably at least 80%, more preferably at least 80% or at least 90%, or 100%) of the polymerase activity observed when the 15 minute incubation prior to the initiation of the DNA polymerase activity assay was done on ice (0° C.), i.e. there is at least 70%, at least 80%, at least 90% or 100% "residual" activity.

Suitable experiments for analysing the temperature stability of DNA polymerases are known in the art any of these may be used. DNA polymerase temperature stability may be assessed by incubating the DNA polymerase at a temperature under test (for example 0° C. (e.g. on ice), 5° C., 10° C., 15° C., 20° C., 25° C., 30° C., 35° C., 37° C., 40° C. or 45° C.) for a period of time (e.g. 5 minutes to 25 minutes, preferably about 15 minutes) prior to performing an assay to determine polymerase activity. Preferably, DNA polymerase stability may be assessed by incubating the DNA polymerase at the temperature under test (for example 0° C. (e.g. on ice), 5° C., 10° C., 15° C., 20° C., 25° C., 30° C., 35° C., 37° C., 40° C. or 45° C.) for 15 minutes and subsequently cooling down the DNA polymerase on ice (e.g. for 5 minutes) prior to performing an assay to determine polymerase activity. Preferably, the DNA polymerase activity is as assessed at about 25° C. (25° C. is preferred). DNA polymerase activity may preferably be assessed using a single-nucleotide incorporation assay, preferably as described elsewhere herein. Particularly preferably, DNA polymerase activity is as assessed in accordance with the single-nucleotide incorporation assay described in the Example section.

Particularly preferred DNA polymerases of the present invention have good stability and also good activity over a broad range of temperatures.

Some DNA polymerases of the present invention have a broad pH stability profile (pH 6.0 to pH 8.5) as assessed by analysing DNA polymerase melting temperature ($T_m$). Some DNA polymerases of the present invention have a melting temperature of about 42° C.–45° C., preferably about 43° C.–44° C. in the pH range 6.0 to 8.5. Melting temperature ($T_m$) may be determined by thermofluor experiments (Ericsson et al., *Anal. Biochem.*, 2006, 357, 289-298). A particularly preferred assay is described in the Example section.

Some DNA polymerases of the present invention have a higher DNA polymerase activity (specific activity) than some commercially available DNA polymerases.

Some DNA polymerases of the present invention have a higher DNA polymerase activity (specific activity) than some commercially available DNA polymerases at a temperature of about 25° C. (25° C. is preferred).

DNA polymerase activity (specific activity) can be analysed using any suitable assay and a skilled person is readily able to select a suitable assay. DNA polymerase activity as discussed herein may be assessed using an isothermal amplification assay. DNA polymerase activity as discussed herein may be assessed using an isothermal molecular beacon assay. In an exemplary molecular beacon assay, a molecular beacon template includes a loop region that is connected by a GC-rich stem region; the molecular beacon template has two fluorophores that are in close proximity and thus quenched; upon extension by the DNA polymerase (DNA polymerase I) of a primer that is annealed to the molecular beacon template the stem is opened and the increase in distance between the two fluorophores is measured by the restoration of the fluorescence of a previously quenched fluorophore.

Thus, DNA polymerase activity may be assessed in an assay having the steps of (i) providing a template DNA molecule (molecular beacon template) which comprises a loop region that is connected by a GC-rich stem region and which comprises two fluorphores that are quenched by virtue of their close proximity to each other, (ii) annealing a primer to said template DNA molecule, (iii) incubating said template-primer complex with a DNA polymerase (e.g. at about 25° C., preferably 25° C.) and (iv) measuring the restoration in fluorescence of a previously quenched fluorophore, wherein said fluorescence is indicative of DNA polymerase activity.

In preferred embodiments, DNA polymerase activity is as assessed at about 25° C. (25° C. is preferred). DNA polymerase activity may be assessed using an isothermal molecular beacon assay that is carried out at about 25° C. (25° C. is preferred).

A preferred molecular beacon template and primer are as described in the Example.

A preferred DNA polymerase activity assay is the polymerase activity assay described in the Example section herein, which is an isothermal molecular beacon assay. Thus, in preferred embodiments DNA polymerase activity is as assessed in accordance with the polymerase activity assay described in the Example section.

Some DNA polymerases of the present invention have a higher polymerase activity (specific activity) than the *E. coli* Klenow fragment DNA polymerase (also referred to herein as KF), the *Geobacillus stearothermophilus* DNA polymerase (also referred to herein as Bst) and/or the commercially available variant of the *G. stearothermophilus* DNA polymerase Bst2.0. Preferably, the DNA polymerase activity is as assessed at about 25° C. (25° C. is preferred). DNA polymerase activity may be assessed using an isothermal molecular beacon assay (e.g. carried out at 25° C.). More preferably, DNA polymerase activity is assessed in accordance with the polymerase activity assay described in the Example section.

Some DNA polymerases of the present invention have at least 50%, at least 75%, at least 100% or at least 150% higher polymerase activity (specific activity) than the *E. coli* Klenow fragment DNA polymerase. Preferably, the DNA polymerase activity is as assessed at about 25° C. (25° C. is preferred). DNA polymerase activity may be assessed using an isothermal molecular beacon assay (e.g. carried out at 25° C.). More preferably, DNA polymerase activity is assessed in accordance with the polymerase activity assay described in the Example section.

Some DNA polymerases of the present invention have at least 50%, at least 75%, at least 100%, at least 150%, at least 200%, at least 500% or at least 1000% higher polymerase activity (specific activity) than the *G. stearothermophilus* DNA polymerase. Preferably, the DNA polymerase activity is as assessed at about 25° C. (25° C. is preferred). DNA polymerase activity may be assessed using an isothermal molecular beacon assay (e.g. carried out at 25° C.). More preferably, DNA polymerase activity is assessed in accordance with the polymerase activity assay described in the Example section.

Some DNA polymerases of the present invention have at least 50%, at least 75%, at least 100%, at least 150%, at least 200%, at least 300%, at least 400% or at least 500% higher polymerase activity (specific activity) than the commercially available variant of *G. stearothermophilus* DNA polymerase (Bst2.0). Preferably, the DNA polymerase activity is as assessed at about 25° C. (25° C. is preferred). DNA polymerase activity may be assessed using an isothermal molecular beacon assay (e.g. carried out at 25° C.). More preferably, DNA polymerase activity is assessed in accordance with the polymerase activity assay described in the Example section.

Some DNA polymerases of the present invention have a higher DNA polymerase activity (specific activity) compared with other marine polymerases (e.g. DNA polymerase from *Aliivibrio Salmonicida*), in particular at a temperature of about 25° C. (25° C. is preferred). Some DNA polymerases of the present invention have at least 10%, at least 20%, at least 30%, at least 40% or at least 50% higher polymerase activity (specific activity) than the DNA polymerase from *Aliivibrio Salmonicida*. Preferably, the DNA polymerase activity is as assessed at about 25° C. (25° C. is preferred). DNA polymerase activity may be assessed using an isothermal molecular beacon assay (e.g. carried out at 25° C.). More preferably, DNA polymerase activity is assessed in accordance with the polymerase activity assay described in the Example section.

Some DNA polymerases of the present invention have a DNA polymerase activity (specific activity) of at least 200,000 mRFU/min/µg, at least 250,000 mRFU/min/µg or at least 300,000 mRFU/min/µg when analysed at 25° C. in accordance with a DNA polymerase activity assay described herein, preferably when analysed in accordance with the DNA polymerase activity assay described in the Example section herein.

Some DNA polymerases of the present invention have a high strand displacement activity. This is an important property as in many isothermal amplification methods success relies on the inherent strand displacement activity of the DNA polymerase used in the reaction setup. The term "strand displacement" describes the ability of the polymerase to displace downstream DNA encountered during synthesis.

Some DNA polymerases of the present invention have a higher strand displacement activity than other commercially available DNA polymerases at a temperature of about 25° C. (preferably 25° C.).

Suitable assays to assess strand displacement activity of a DNA polymerase are known in the art and a skilled person is readily able to select a suitable assay. In an exemplary strand displacement activity assay, a "cold" primer and a reporter strand that is labelled with a fluorophore (e.g. TAMRA) at its 3' end are annealed to a template strand that has a quencher (e.g. BHQ2) at its 5' end (the fluorophore is thus quenched by the close proximity of the quencher) such that there is a one nucleotide gap between the 3' end of the annealed primer and the 5' end of the annealed reporter strand; upon strand displacement activity of the DNA polymerase the fluorophore labelled oligonucleotide (reporter strand) is displaced from the template strand and as a consequence the fluorophore and quencher are no longer in close proximity and an increase in fluorescence can be measured.

Strand displacement activity may be assessed in an assay having the steps of (i) providing a template DNA molecule that has a quencher (fluorescence quencher) at its 5' end, (ii) annealing to said template DNA molecule a cold primer (i.e. non-fluorescent oligonucleotide) and a reporter strand (reporter oligonucleotide) that is labelled with a fluorophore at its 3' end wherein there is a one nucleotide gap between the 3' end of the annealed primer and the 5' end of the annealed reporter strand, whereby the quencher quenches the fluorophore by virtue of their close proximity to each other, (iii) incubating said template-cold primer-reporter strand complex with a DNA polymerase (e.g. at about 25° C., preferably 25° C.) and (iv) measuring the fluorescence of the previously quenched fluorophore, wherein said fluorescence is indicative of strand displacement activity.

In preferred embodiments, strand displacement is as assessed in an assay that is carried out at 25° C.

Preferred primers, reporter strands and template strands are as described in the Example.

In a preferred embodiment strand displacement activity is as assessed in accordance with the strand displacement activity assay described in the Example section.

Some DNA polymerases of the present invention have at least 50%, at least 75%, at least 100%, at least 150%, at least 200%, at least 500%, at least 1000% or at least 2000% higher strand displacement activity than the *E. coli* Klenow fragment DNA polymerase. Preferably, the strand displacement activity is as assessed at about 25° C. (25° C. is preferred). Strand displacement activity may be assessed using a strand displacement assay as described herein (e.g. carried out at 25° C.). More preferably, strand displacement activity is assessed in accordance with the strand displacement assay described in the Example section.

Some DNA polymerases of the present invention have at least 50%, at least 75%, at least 100%, at least 150%, at least 200%, at least 500, at least 600% or at least 700% higher strand displacement activity than the *G. stearothermophilus* DNA polymerase. Preferably, the strand displacement activity is as assessed at about 25° C. (25° C. is preferred). Strand displacement activity may be assessed using a strand displacement assay as described herein (e.g. carried out at 25° C.). More preferably, strand displacement activity is assessed in accordance with the strand displacement assay described in the Example section.

Some DNA polymerases of the present invention have at least 50%, at least 75%, at least 100%, at least 150%, at least 200% or at least 400% higher strand displacement activity than the commercially available variant of *G. stearothermophilus* DNA polymerase (Bst2.0). Preferably, the strand displacement activity is as assessed at about 25° C. (25° C. is preferred). Strand displacement activity may be assessed using a strand displacement assay as described herein (e.g. carried out at 25° C.). More preferably, strand displacement activity is assessed in accordance with the strand displacement assay described in the Example section.

Some DNA polymerases of the present invention have a higher strand displacement activity compared with other marine polymerases (e.g. DNA polymerase from *Aliivibrio Salmonicida*). Some DNA polymerases of the present invention have a higher strand displacement activity than other marine DNA polymerases at a temperature of about 25° C. (25° C. is preferred). In some embodiments, DNA polymerases of the present invention have at least 50%, at least 75%, at least 100%, at least 150%, at least 200% or at least 500% higher strand displacement than the DNA polymerase from *Aliivibrio Salmonicida*. Preferably, the strand displacement activity is as assessed at about 25° C. (25° C. is preferred). Strand displacement activity may be assessed using a strand displacement assay as described herein (e.g. carried out at 25° C.). More preferably, strand displacement activity is assessed in accordance with the strand displacement assay described in the Example section.

Some DNA polymerases of the present invention have a strand displacement activity of at least 20,000 mRFU/min/µg, at least 25,000 mRFU/min/µg or at least 30,000 mRFU/min/µg when analysed at 25° C. in accordance with a strand displacement activity assay described herein, preferably in accordance with the strand displacement activity assay in the Example section herein.

Preferred DNA polymerases of the present invention have high processivity. "Processivity" in the context of DNA polymerases is the ability of a DNA polymerase to remain bound to the DNA template strand during synthesis (nucleotide incorporation) before dissociating, and the overall efficiency of DNA synthesis may therefore increase with increasing processivity of a given polymerase. Put another way, processivity represents a measure of the average number of nucleotides added by a DNA polymerase, per association event with the template strand. A DNA polymerase with high processivity may be of particular importance if longer stretches of DNA need to be synthesized.

Some DNA polymerases of the present invention have higher processivity than the commercial *G. stearothermophilus* DNA polymerase (BstpolI, Bst2.0) and *Bacillus subtilis* DNA polymerase (also referred to herein as BSU). In preferred embodiments, the higher processivity is significantly higher. In some preferred embodiments the DNA polymerases of the present invention have at least 10%, at least 20%, at least 30%, at least 40%, at least 50%, at least 75%, at least 100%, at least 200%, at least 500%, at least 1000%, at least 1500% or at least 2000% higher processivity than the commercial *G. stearothermophilus* DNA polymerase (BstpolI, Bst2.0) and/or the *B. subtilis* DNA polymerase (also referred to herein as BSU).

Some DNA polymerases of the present invention have at least 5000%, at least 10,000%, at least 15,000%, at least 20,000%, at least 25,000% or at least 30,000% higher processivity than the commercial *G. stearothermophilus* DNA polymerase (BstpolI, Bst2.0).

Some DNA polymerases of the present invention have at least 1000%, at least 1500% or at least 2000% higher processivity than the *B. subtilis* DNA polymerase (also referred to herein as BSU).

Suitable assays for analysing processivity are well known in the art. A suitable and particularly preferred processivity assay is described herein in the Example section.

Preferred DNA polymerases of the present invention have useful levels of polymerase activity across a range of salt (NaCl) concentrations. Put another way, DNA polymerases of the present invention exhibit across a broad range of salt concentrations a substantial proportion of the DNA polymerase activity observed at the salt concentration at which maximum polymerase activity is observed. Suitable assays for determining DNA polymerase activity are described elsewhere herein. A preferred assay for determining DNA polymerase activity is an isothermal molecular beacon assay, e.g. as described herein, preferably as described in the Example section.

In some embodiments, the NaCl concentration at which the DNA polymerase exhibits its maximum activity is about 65 mM to 100 mM (e.g. 70, 75, 80, 85 or 90 mM).

In some embodiments, across a concentration range from about 0 mM to 210 mM NaCl, DNA polymerases of the present invention exhibit a substantial proportion (e.g. at least 30%) of their maximum polymerase activity.

In some embodiments, across a concentration range from about 20 mM to 150 mM NaCl, DNA polymerases of the present invention exhibit at least 60% of their maximum polymerase activity.

In some embodiments, across a concentration range from about 60 mM to 120 mM NaCl, DNA polymerases of the present invention exhibit at least 80% (preferably at least 90% or at least 95%) of their maximum polymerase activity.

Preferably, the above described abilities and properties are observed at a measurable or significant level and more preferably at a statistically significant level, when compared to appropriate control levels. Appropriate significance levels are discussed elsewhere herein. More preferably, one or more of the above described abilities and properties are observed at a level which is measurably better, or more preferably significantly better, when compared to the abilities observed for prior art DNA polymerases.

In another aspect, the present invention provides an isolated DNA polymerase comprising (or consisting of) the amino acid sequence of SEQ ID NO:1 or comprising (or consisting of) an amino acid sequence which is at least 70% identical to SEQ ID NO:1, wherein said DNA polymerase lacks a 5'-3' exonuclease domain (e.g. lacks some or all of the amino acid sequence of SEQ ID NO:5). Other features and properties of other aspects of the invention apply, mutatis mutandis, to this aspect of the invention.

In yet another aspect, the present invention provides an isolated DNA polymerase comprising (or consisting of) the amino acid sequence of SEQ ID NO:1 or comprising (or consisting of) an amino acid sequence which is at least 70% identical to SEQ ID NO:1, wherein said DNA polymerase is not a wildtype DNA polymerase from a *Psychrobacillus* sp. Other features and properties of other aspects of the invention apply, mutatis mutandis, to this aspect of the invention.

In a further aspect the present invention provides molecules (e.g. proteins) comprising DNA polymerases of the present invention.

As used throughout the entire application, the terms "a" and "an" are used in the sense that they mean "at least one", "at least a first", "one or more" or "a plurality" of the referenced components or steps, except in instances wherein an upper limit or exclusion is thereafter specifically stated. The operable limits and parameters of combinations, as with the amounts of any single agent, will be known to those of ordinary skill in the art in light of the present disclosure.

Nucleic acid molecules comprising nucleotide sequences that encode DNA polymerases of the present invention as defined herein or fragments thereof, or nucleic acid molecules substantially homologous thereto, form yet further aspects of the invention. A preferred nucleic acid molecule is a nucleic acid encoding the *Psychrobacillus* species DNA polymerase I sequence of SEQ ID NO:1, or a sequence substantially homologous thereto. A preferred nucleic acid molecule comprises (or consists of) the nucleotide sequence as set forth in SEQ ID NO:2, or is a sequence substantially homologous thereto. Optionally, the final three nucleotides of SEQ ID NO:2 may be omitted. Nucleic acid sequences of the invention include sequences having at least 70% or 75%, preferably at least 80%, and even more preferably at least 85%, 90%, 95%, 96%, 97%, 98%, 99% or 99.5%, sequence identity to SEQ ID NO:2. Nucleic acid sequences of the invention thus include single or multiple base alterations (additions, substitutions, insertions or deletions) to the sequence of SEQ ID NO:2.

A particularly preferred nucleic acid molecule comprises the nucleotide sequence as set forth in SEQ ID NO:2.

Another preferred nucleic acid molecule consists of the nucleotide sequence as set forth in SEQ ID NO:2.

The present invention also extends to nucleic acid molecules comprising (or consisting of) nucleotide sequences which are degenerate versions of nucleic acid molecules described herein, e.g. degenerate versions of a nucleic acid molecule comprising (or consisting of) SEQ ID NO:2.

Nucleic acid molecules of the invention are preferably "isolated" or "purified".

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA*, 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS*, 4:11-17, 1988), FASTA (Pearson and Lipman, *Proc. Natl. Acad. Sci. USA*, 85:2444-2448, 1988; Pearson, Methods in Enzymology, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose. Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

A "conservative amino acid substitution", as used herein, is one in which the amino acid residue is replaced with another amino acid residue having a similar side chain. Families of amino acid residues having similar side chains have been defined in the art.

DNA polymerases of the present invention comprise genetically encoded amino acids, but may also contain one or more non-genetically encoded amino acids.

In addition to having DNA polymerase activity, variants or enzymatically active fragments of DNA polymerases of the invention described herein preferably have one or more of the other properties described herein, more preferably all of the other properties described herein.

The term "isolated" or "purified" as used herein in reference to nucleic acid molecules or sequences and proteins or polypeptides, e.g., DNA polymerases, refers to such molecules when isolated from, purified from, or substantially free of their natural environment, e.g., isolated from or purified from an organism (if indeed they occur naturally), or refers to such molecules when produced by a technical process, i.e., includes recombinant and synthetically produced molecules.

Thus, when used in connection with a protein or polypeptide molecule such as a DNA polymerase, the term "isolated" or "purified" typically refers to a protein substantially free of cellular material or other proteins from the source from which it is derived. In some embodiments, such isolated or purified proteins are substantially free of culture medium when produced by recombinant techniques, or chemical precursors or other chemicals when chemically synthesized.

Possible expression vectors include but are not limited to cosmids or plasmids, so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

In one aspect the present invention therefore provides an expression vector (preferably a recombinant expression vector) containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and *Maniatis, Molecular Cloning: A Laboratory Manual*, 2nd Ed., Cold Spring Harbor Press, Cold Spring Harbor, N.Y., 1989) and other laboratory textbooks.

Suitable host cells include a wide variety of prokaryotic host cells and eukaryotic cells. Preferably, proteins of the invention may be expressed in bacterial host cells, such as *Escherichia coli*.

N-terminal or C-terminal fusion proteins comprising DNA polymerases and proteins of the invention conjugated to other molecules, such as proteins (e.g. epitope tags), may be prepared by fusing through recombinant techniques.

A yet further aspect provides a host cell or virus comprising one or more expression constructs or expression vectors of the invention. Also provided are host cells or viruses comprising one or more of the nucleic acid molecules of the invention. A host cell or virus capable of expressing a DNA polymerase of the invention forms a yet further aspect. Preferred host cells include Rosetta 2 (DE3) cells (Novagen).

Where appropriate, DNA polymerases of the invention may be isolated from a natural source, e.g. isolated from extracts of a *Psychrobacillus*, or produced recombinantly in a host cell and isolated and purified therefrom. The DNA polymerases of the invention may therefore be recombinant enzymes, in particular isolated recombinant enzymes. In certain embodiments the DNA polymerase is produced by recombinant techniques in a host cell that is not, or not from, an organism which is the same as that in which the DNA polymerase is found naturally, i.e. a heterologous host cell.

DNA polymerases of the present invention may be generated using recombinant DNA technology. Alternatively, a cell-free expression system can be used for production of the DNA polymerase. Alternatively, DNA polymerases of the present invention may be generated using chemical synthesis so that the DNA polymerase is generated by stepwise elongation, one amino acid at a time. Such chemical synthesis techniques (e.g. solid phase synthesis) are well known in the chemistry of proteins.

A further aspect of the invention provides a method of producing a DNA polymerase of the present invention comprising a step of culturing the host cells of the invention.

Preferred methods comprise the steps of (i) culturing a host cell comprising one or more of the recombinant expression vectors or one or more of the nucleic acid molecules of the invention under conditions suitable for the expression of the encoded DNA polymerase or protein; and optionally (ii) isolating or obtaining the DNA polymerase or protein from the host cell or from the growth medium/supernatant. Such methods of production may also comprise a step of purification of the DNA polymerase or protein product and/or formulating the DNA polymerase or product into a composition including at least one additional component, such as an acceptable buffer or carrier.

The DNA polymerase may be separated, or isolated, from the host cells/culture media using any of the purification techniques for protein known in the art and widely described in the literature or any combination thereof. Such techniques may include for example, precipitation, ultrafiltration, dialysis, various chromatographic techniques, e.g. size exclusion chromatography, ion-exchange chromatography, affinity chromatography, electrophoresis, centrifugation etc. As discussed above, the DNA polymerase of the invention may be modified to carry amino acid motifs or other protein or non-protein tags, e.g. polyhistidine tags (e.g. $His_6$-tag), to assist in isolation, solubilisation and/or purification or identification.

A preferred method of producing a DNA polymerase of the invention is described in the Example section herein.

In another aspect, the present invention provides the use of a DNA polymerase of the invention for nucleotide (e.g. dNTP) polymerisation. Accordingly, DNA polymerases of the invention may be used to extend a nucleic acid (DNA) strand by one or more nucleotides.

In another aspect, the present invention provides the use of a DNA polymerase of the invention in a nucleic acid (DNA) amplification or sequencing reaction.

In another aspect, the present invention provides the use of a DNA polymerase of the invention in a molecular beacon assay, or in a strand displacement assay or in a single-nucleotide incorporation assay, e.g. as described herein.

Preferably, in uses and methods of the present invention, DNA polymerases of the present invention are used at a constant temperature, i.e. without thermal cycling. Accordingly, the use of DNA polymerases of the invention in isothermal reactions is particularly preferred. The use of DNA polymerases of the invention in isothermal amplification reactions is particularly preferred. Isothermal reactions are performed at a constant temperature. Many isothermal amplification techniques are known in the art and include Loop mediated isothermal amplification (LAMP), rolling circle amplification (RCA), strand displacement amplification (SDA), multiple displacement amplification (MDA) and cross priming amplification (CPA).

In another aspect, the present invention provides a method of nucleotide polymerisation using a DNA polymerase of the present invention. Preferably, said method comprises providing a reaction mixture comprising a DNA polymerase of the present invention, a template nucleic acid molecule, an oligonucleotide primer which is capable of annealing to a portion of the template nucleic acid molecule and one or more species of nucleotide (e.g. deoxynucleoside triphosphates, dNTPS) and incubating said reaction mixture under conditions whereby the oligonucleotide primer anneals to the template nucleic acid molecule and said DNA polymerase extends said oligonucleotide primer by polymerising one or more nucleotides. Suitable conditions are well known in the art. Preferably a constant temperature is used and preferred temperatures are set out elsewhere herein. Optionally, the generation of the polynucleotide product is detected (e.g. via gel electrophoresis).

In another aspect, the present invention provides a method of amplifying a nucleic acid (DNA) using a DNA polymerase of the present invention. Typically, said method comprises providing a reaction mixture comprising a DNA polymerase of the present invention, a template nucleic acid molecule, an oligonucleotide primer(s) (e.g. 2 or more primers such as 2, 3, 4, 5 or 6 primers) which is capable of annealing to a portion of the template nucleic acid molecule acid molecule, and nucleotides (e.g. deoxynucleoside triphosphates, dNTPS) and incubating said reaction mixture under conditions whereby the oligonucleotide primer(s) anneals to the template nucleic acid molecule and said DNA polymerase extends said oligonucleotide primer(s) by polymerising one or more nucleotides to generate a polynucleotide. Suitable conditions are well known in the art. Preferred methods of nucleic acid amplification are isothermal amplification methods. Isothermal amplification methods of the invention are performed at a constant temperature and preferred temperatures are set out elsewhere herein. Optionally, the generation of the polynucleotide product is detected (e.g. via gel electrophoresis).

Exemplary isothermal amplification methods include Loop mediated isothermal amplification (LAMP), rolling circle amplification (RCA), strand displacement amplification (SDA), multiple displacement amplification (MDA) and cross priming amplification (CPA).

Preferably, the constant temperature used in the methods and uses of the present invention is a low-to-moderate temperature, for example, 0° C. to about 42° C., preferably about 10° C. to about 40° C., or about 20° C. to about 40° C., or about 25° C. to about 40° C., or about 30° C. to about 40° C. or about 35° C. to about 40° C., or about 37° C. to about 40° C. In some embodiments, the constant temperature is about 10° C. to about 15° C. or is about 10° C. to about 20° C. In some embodiments, the constant temperature is about 10° C. to about 30° C. In some embodiments, the constant temperature is about 20° C. to about 30° C. In some embodiments, the constant temperature is about 10° C. to about 25° C. In some embodiments, the constant temperature is about 20° C. to about 25° C. A constant temperature of about 25° C. is preferred. In some embodiments, the constant temperature is 25° C.

A temperature may be considered constant when no active steps are taken to modify the temperature during the reaction, e.g. no thermal cycling. A 'constant' temperature may still allow temperature fluctuations during the method of up to about 5° C., typically no more than 3° C. or 2° C.

DNA polymerases of the present invention may be used in point-of-care molecular diagnostics platforms.

DNA polymerases of the present invention may be used in whole genome amplification.

DNA polymerases of the present invention may be used in next-generation sequencing methods. So-called "next generation" or "second generation" sequencing approaches (in reference to the Sanger dideoxynucleotide method as the "first generation" approach) have become widespread. These newer techniques are characterised by high throughputs, e.g. as a consequence of the use of parallel, e.g. massively parallel sequencing reactions, or through less time-consuming steps. Various high throughput sequencing methods provide single molecule sequencing and employ techniques such as pyrosequencing, reversible terminator sequencing, cleavable probe sequencing by ligation, noncleavable probe sequencing by ligation, DNA nanoballs, and real-time single molecule sequencing.

Uses and methods employing enzymatically active fragments of DNA polymerases of the invention are also provided and references herein to DNA polymerases of the invention encompass such active fragments unless otherwise clear from the context.

Uses and methods of the present invention are typically performed in vitro.

The present invention also provides compositions comprising a DNA polymerase of the invention. Such compositions preferably comprise a buffer. Optionally, compositions of the present invention further comprise one or more of the necessary reagents to carry out a nucleic acid amplification reaction (e.g. an isothermal amplification reaction), e.g. oligonucleotide primers capable of annealing to a region of the template DNA to be amplified and/or nucleotides (e.g. dNTPs). Typically compositions will be aqueous and buffered with a standard buffer such as Tris, HEPES, etc.

The invention further includes kits comprising one or more of the DNA polymerases of the invention, or one or more compositions of the invention, or one or more of the nucleic acid molecules of the invention, or one or more expression vectors of the invention, or one or more host cells or viruses of the invention. Preferably said kits are for use in the methods and uses as described herein, e.g., in nucleic acid amplification methods, such as isothermal amplification reactions. Preferably said kits comprise instructions for use of the kit components, for example for nucleic acid amplification.

Nucleotide and Amino Acid Sequences Disclosed Herein and their Sequence Identifiers (SEQ ID NOS)

All nucleotide sequences are recited herein 5' to 3' in line with convention in this technical field.

SEQ ID NO:1—amino acid sequence of truncated DNA polymerase I isolated from a *Psychrobacillus* sp.

```
                                                    SEQ ID NO: 1
TEVAFEIVEEIDSTILDKVMSVHLEMYDGQYHTSELLGIALSDGEKGYFA

PADIAFQSKDFCSWLENATNKKYLADSKATQAVSRKHNVNVHGVEFDLLL

AAYIVNPAISSEDVAAIAKEFGYFNLLTNDSVYGKGAKKTAPEIEKIAEH

AVRKARAIWDLKEKLEVKLEENEQYALYKEIELPLASILGTMESDGVLVD

KQILVEMGHELNIKLRAIEQDIYALAGETFNINSPKQLGVILFEKIGLTP

IKKTKTGYSTAADVLEKLASEHEIIEQILLYRQLGKLNSTYIEGLLKEIH

EDDGKIHTRYQQALTSTGRLSSINPNLQNIPVRLEEGRKIRKAFVPSQPG

WVMFAADYSQIELRVLAHMSEDENLVEAFNNDLDIHTKTAMDVFHVEQEA

VTSDMRRAAKAVNFGIVYGISDYGLSQNLDITRKEAATFIENYLNSFPGV

KGYMDDIVQDAKQTGYVTTILNRRRYLPEITSSNFNLRSFAERTAMNTPI

QGSAADIIKKAMIDMAERLISENMQTKMLLQVHDELIFEAPPEEIAMLEK

IVPEVMENAIKLIVPLKVDYAFGSSWYDTK
```

SEQ ID NO:2—nucleic acid sequence encoding the *Psychrobacillus* species DNA polymerase I sequence of SEQ ID NO:1

```
                                                    SEQ ID NO: 2
acagaagtagcattcgagattgttgaagaaattgactctacaatattaga taaagtaatgtcagtccatttagaaatgtatgatgggcaatatcatacaa
```

```
                                                    -continued
gcgaattattaggtattgctttatcagatggagaaaagggttattttgct cctgctgatatagcttttcaatcgaaggattttgttcttggttagaaaa tgctacgaataaaaagtatttagcagactccaaagcaacacaagcagtga gtagaaaacataatgtgaatgtacatggagtggaattcgaccttctttta gcagcgtatatagtaaatcctgctatctcttcagaggatgttgctgctat tgctaaagaatttggatatttttaacttgctgacaaacgatagtgtttatg ggaaaggtgccaaaaaaaccgcacctgaaatcgagaaaattgcagaacat gccgtaagaaaagcaagggctatttgggacttgaaagaaaagttagaagt aaaactggaagaaaatgaacaatatgcgttgtataaagaaatagagctac cgcttgcatctatccttggtacgatggaatcagatggggtgctggtggat aaacaaattcttgtagaaatgggtcatgagcttaatattaagttacgagc gattgaacaagacatttatgcgttagctggtgaaacgtttaatattaatt caccttaaacaattaggtgtaatactatttgaaaaaattggtcttacccct attaaaaagacaaaaacgggctattcaactgcagcagatgttttggaaaa actagcaagtgaacatgaaataatagagcaaattttactatatcgtcaat taggtaaactcaattccacatatatcgaaggattattaaaagagattcat gaagatgatgggaagatccatacccgatatcaacaagccctaacttcaac tgggcgtttgagttcgatcaatccaaaccttcaaaatataccagttcgtt tagaagaaggtagaaaaatacgtaaagcctttgttccttcacaaccggga tgggtaatgtttgcggcggattactctcaaattgaattgcgtgttcttgc ccatatgtctgaggatgaaaacctggtagaagcttttaataatgatctgg atattcatactaaaacggctatggatgtattccatgtggagcaggaagca gtaacgtccgatatgcgccgtgctgctaaggcagttaactttgggattgt gtatggtattagtgattatggtttatcacaaaacctagatattactgaaa aagaagcggcgacattatcgagaatttattaaatagcttcccaggtgta aaaggatatatggatgatatcgttcaagatgcgaaacaaacaggctacgt tacaacaattttgaatagacgaagatatttgcctgaaataacaagttcta actttaatctccgcagttttgcagaacgtactgctatgaatacaccaatt caagggagtgcagccgatattattaaaaaagcaatgatcgatatggcgga aagattaatatcagaaaatatgcagaccaaaatgctactacaagtacatg atgaattaattttgaggctccaccagaggaaattgcaatgctagaaaaa atagtgccagaggtgatggaaaacgctattaaactgattgtacctttgaa agtggattatgcctttggttcatcttggtatgacacgaagtag
```

SEQ ID NO:3—amino acid sequence of full-length DNA polymerase I isolated from a *Psychrobacillus* sp.

```
                                                    SEQ ID NO: 3
MYLSTEKILLLDGNSLAYRAFFALPLLTNEHGIHTNAVYGFTMMLQKIMD

EENPTHMLVAFDAGKTTFRHSTFGDYKGGRQKTPPELSEQFPYIRKLIDA

YGIKRYELEMYEADDIIGTLSKRADEKGQQVVIVSGDKDLTQLATDKTTV

YITRKGITDIEKYTPEHVQEKYGLTPLQIIDMKGLMGDASDNIPGVPGVG

EKTAIKLLKEHGSVEDLYKALDTVSGVKLKEKLIANEEQAIMSKALATIE
```

-continued

```
TAAPIQISIDDLSYTGPNMEEVIEVWKELAFKTLLEKSDYISEESETTEV

AFEIVEEIDSTILDKVMSVHLEMYDGQYHTSELLGIALSDGEKGYFAPAD

IAFQSKDFCSWLENATNKKYLADSKATQAVSRKHNVNVHGVEFDLLLAAY

IVNPAISSEDVAAIAKEFGYFNLLTNDSVYGKGAKKTAPEIEKIAEHAVR

KARAIWDLKEKLEVKLEENEQYALYKEIELPLASILGTMESDGVLVDKQI

LVEMGHELNIKLRAIEQDIYALAGETFNINSPKQLGVILFEKIGLTPIKK

TKTGYSTAADVLEKLASEHEIIEQILLYRQLGKLNSTYIEGLLKEIHEDD

GKIHTRYQQALTSTGRLSSINPNLQNIPVRLEEGRKIRKAFVPSQPGWVM

FAADYSQIELRVLAHMSEDENLVEAFNNDLDIHTKTAMDVFHVEQEAVTS

DMRRAAKAVNFGIVYGISDYGLSQNLDITRKEAATFIENYLNSFPGVKGY

MDDIVQDAKQTGYVTTILNRRRYLPEITSSNFNLRSFAERTAMNTPIQGS

AADIIKKAMIDMAERLISENMQTKMLLQVHDELIFEAPPEEIAMLEKIVP

EVMENAIKLIVPLKVDYAFGSSWYDTK
```

SEQ ID NO:4—nucleic acid sequence encoding the *Psychrobacillus* sp. DNA polymerase I sequence of SEQ ID NO:3.

SEQ ID NO: 4

```
atgtatttgtcaaccgagaaaatcctattattagacggcaatagtttggc
ataccgagctttttttgccctacctttattaacaaatgaacatggaatac
atacaaacgcagtatatggctttacaatgatgctacaaaaaattatggat
gaagaaaatcctactcatatgctcgtggcatttgatgccgggaaaacgac
cttccgtcactctacttttggggattataaaggtggaagacaaaaaacac
caccagaactatcggaacaattcccttatatacgcaagttaatcgatgct
tatggtattaagcgatacgaactggaaatgtacgaagcagacgatattat
cggtactttaagcaagcgtgcagacgaaaaagggcagcaagttgtaattg
tctcaggtgataaagatttaacacaactagctacagataaaacaactgtg
tatatcacaagaaaaggcataaccgatattgaaaaatatacacctgaaca
tgtacaagaaaagtatggcttaactccattacagattatagacatgaaag
gtttaatgggagatgcttctgataatattccaggagttcctggtgtcgga
gaaaaaacagctattaagcttttaaaagaacatggttcggtagaggattt
atataaagcacttgatacagttagtggtgttaaactaaaggaaaaactca
tcgccaacgaagagcaggcaattatgagtaaggcattagctacgattgaa
acagctgcaccgatacagatttctatagacgatctttcatatactggtcc
taatatggaagaagtaattgaagtttggaaggaactagcttttaaaactc
ttcttgagaaatctgactatatttctgaggaatccgaaactacagaagta
gcattcgagattgttgaagaaattgactctacaatattagataaagtaat
gtcagtccatttagaaatgtatgatgggcaatatcatacaagcgaattat
taggtattgctttatcagatggagaaaagggttattttgctcctgctgat
atagcttttcaatcgaaggatttttgttcttggttagaaaatgctacgaa
taaaaagtatttagcagactccaaagcaacacaagcagtgagtagaaaac
ataatgtgaatgtacatggagtggaattcgaccttcttttagcagcgtat
atagtaaatcctgctatctcttcagaggatgttgctgctattgctaaaga
atttggatattttaacttgctgacaaacgatagtgtttatgggaaaggtg
ccaaaaaaaccgcacctgaaatcgagaaaattgcagaacatgccgtaaga
aaagcaagggctatttgggacttgaaagaaaagttagaagtaaaactgga
agaaaatgaacaatatgcgttgtataaagaaatagagctaccgcttgcat
ctatccttggtacgatggaatcagatggggtgctggtggataaacaaatt
cttgtagaaatgggtcatgagcttaatattaagttacgagcgattgaaca
agacatttatgcgttagctggtgaaacgtttaatattaattcacctaaac
aattaggtgtaatactatttgaaaaaattggtcttacccctattaaaaag
acaaaaacgggctattcaactgcagcagatgttttggaaaaactagcaag
tgaacatgaaataatagagcaaattttactatatcgtcaattaggtaaac
tcaattccacatatatcgaaggattattaaaagagattcatgaagatgat
gggaagatccatacccgatatcaacaagccctaacttcaactgggcgttt
gagttcgatcaatccaaaccttcaaaatataccagttcgtttagaagaag
gtagaaaaatacgtaaagcctttgttccttcacaaccgggatgggtaatg
tttgcggcggattactctcaaattgaattgcgtgttcttgcccatatgtc
tgaggatgaaaacctggtagaagcttttaataatgatctggatattcata
ctaaaacggctatggatgtattccatgtggagcaggaagcagtaacgtcc
gatatgcgccgtgctgctaaggcagttaactttgggattgtgtatggtat
tagtgattatggtttatcacaaaacctagatattactagaaaagaagcgg
cgacatttatcgagaattatttaaatagcttcccaggtgtaaaaggatat
atggatgatatcgttcaagatgcgaaacaaacaggctacgttacaacaat
tttgaatagacgaagatatttgcctgaaataacaagttctaactttaatc
tccgcagttttgcagaacgtactgctatgaatacaccaattcaagggagt
gcagccgatattattaaaaaagcaatgatcgatatggcggaaagattaat
atcagaaaatatgcagaccaaaatgctactacaagtacatgatgaattaa
tttttgaggctccaccagaggaaattgcaatgctagaaaaaatagtgcca
gaggtgatggaaaacgctattaaactgattgtacctttgaaagtggatta
tgcctttggttcatcttggtatgacacgaagtag
```

SEQ ID NO:5—sequence containing a 5'-3' exonuclease functional domain of DNA polymerase I isolated from a *Psychrobacillus* sp.

SEQ ID NO: 5

```
MYLSTEKILLLDGNSLAYRAFFALPLLTNEHGIHTNAVYGFTMMLQKIMD
EENPTHMLVAFDAGKTTFRHSTFGDYKGGRQKTPPELSEQFPYIRKLIDA
YGIKRYELEMYEADDIIGTLSKRADEKGQQVVIVSGDKDLTQLATDKTTV
YITRKGITDIEKYTPEHVQEKYGLTPLQIIDMKGLMGDASDNIPGVPGVG
EKTAIKLLKEHGSVEDLYKALDTVSGVKLKEKLIANEEQAIMSKALATIE
TAAPIQISIDDLSYTGPNMEEVIEVWKELAFKTLLEKSDYISEESET
```

SEQ ID NO:6—amino acid sequence of the truncated DNA polymerase of *Aliivibrio salmonicida* used in experiments described herein.

SEQ ID NO: 6
VDRSKYETIFTKEAFSAWLEKVNNAEVTAFDTETDSLDYMVANLIGLSFS

VEEGEAAYVPVAHDYLDAPEQLDRDWVLAQLKPYLEDETKAKVGQNLKYD

ASVLARYDIEMKGIKFDTMLESYVYNSVAGKHNMDSLALRYLQHNTISFE

EIAGKGKKQLTFNQIALEEAAPYAAEDADITLRLHNVLHAKLVTDEKLNA

VFTDIELPLISVLSRMERKGVYIDDMLLSAQSLEIGQRLDELETASFEVA

GQEFNMNSPKQLQTILFEKMELPVIKKTPSGAASTNEEVLQELALEYELP

KLILEYRGLAKLKSTYTDKLPKMINPSTGRVHTSYHQAVTATGRLSSTDP

NLQNIPIRNKEGRRIRQAFVAPHGWKILAVDYSQIELRIMAHLSQDRALL

EAFSAGKDIHAATAAEVKGVSIEEVTSEDRRRAKAINFGLIYGMSAFGLA

KQIGISRGEAQDYMNVYFERYPGVMQYMEETRLLATEQGYVETLYGRRLY

LPEINARNAIRRKAAERAAINAPMQGTAADIIKKAMILVDNWIEAEGTGR

VNLLMQVHDELVFEVKEDELEAITKQVTALMEAAVSLDVPLIAESGFGDN

WDEAH

Commercial enzymes used for comparison with the PB DNA polymerase, namely KF, Bst, Bst2.0, BSU, T4 and T7 DNA polymerase are all bought from New England Biolabs.

The invention will now be described by way of non-limiting Example with reference to the following figures in which:

FIG. 1 shows a comparison of the polymerase activity at 25° C. (specific activity) of the recombinantly produced marine polymerase from a *Psychrobacillus* sp. (PB) with other polymerases. The commercially known polymerases are KF (Klenow Fragment *E. coli*), Bst (*G. stearothermophilus*), Bst 2.0 (*G. stearothermophilus*) and BSU (*B. subtilis*).

FIG. 2 shows an overview of the strand-displacement activity assay setup. F=fluorophore. Q=Quencher.

Figure 8:
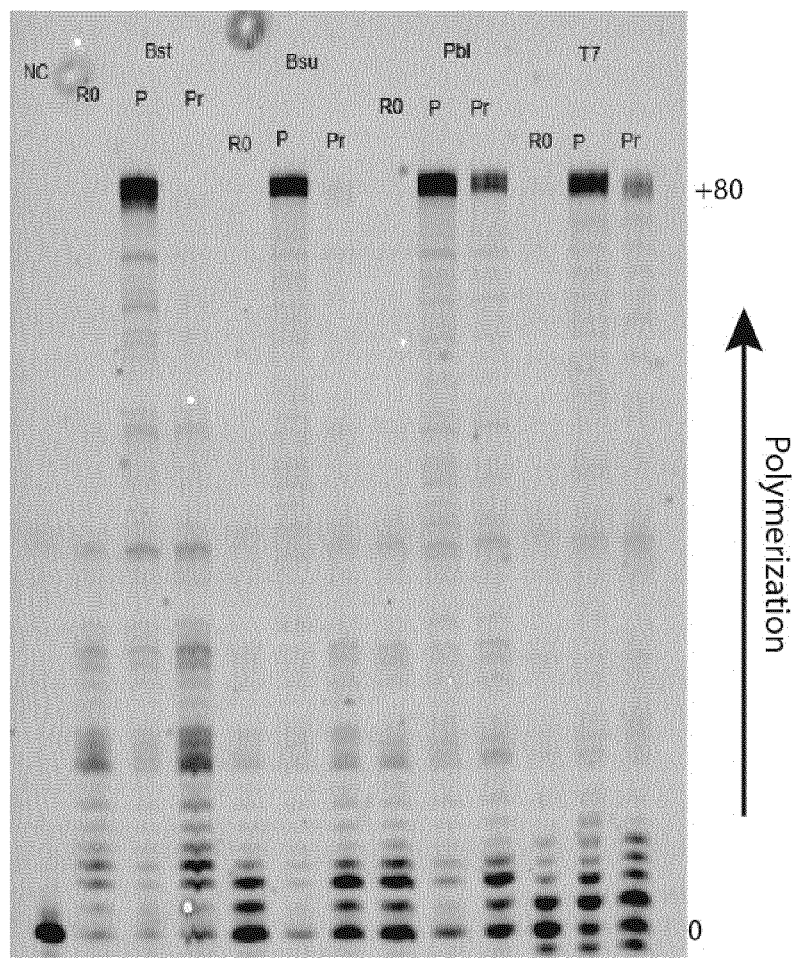

FIG. 8 shows a comparison of processivity (lanes marked Pr) between the commercial thermophilic BstpolI (Bst2.0), mesophilic Bsu and PB polI (Pbl). T7 is a known high processivity enzyme and is used as a positive control for high processivity. Lanes marked with P indicate the polymerase activity while Pr indicates processivity. Processivity is analysed based on the incubation of a non-labeled DNA trap, which will out compete rebinding of the DNA polymerase to the labeled substrate if the enzyme dissociates from the template strand and less final product yield (+80 nucleotide incorporations) can be seen on the gel.

EXAMPLE

Cloning, Gene Expression and Protein Purification

Production of PB Polymerase of SEQ ID NO:1

Based on structural knowledge of *Geobacillus stearothermophilus* DNA polymerase I and its truncated "large fragment" (PDB 1 L3S), the unwanted 5"-3"-exonuclease domain has been removed in the expression constructs, i.e. the Forward primer is designed in such a way that the PCR product of the PB polymerase lacks the unwanted exonuclease domain. The gene encoding the DNA polymerase I from the *Psychrobacillus* sp. was cloned into the vector pET151/D-TOPO® using the Gateway® Technology (Thermo Fisher). The starting material for the polymerase chain reaction was the genomic DNA of *Psychrobacillus* sp. By the use of the forward primer (5'-CACCACAGAAGTAGCATTCGAGATTGTT-3' (SEQ ID NO:7)) and reverse primer (5'-TTACTTCGTGTCATACCAAGATGAACC-3' (SEQ ID NO:8)) the gene has been truncated and is analogous to the so-called large fragment of the polymerase I.

Recombinant protein production was performed in Rosetta 2 (DE3) cells (Novagen®). The cells grew in Terrific Broth and gene expression was induced by addition of IPTG. Protein production was carried out at 15° C. for 6 h. In the first purification step the $His_6$-tagged protein was purified by immobilized $Ni^{2+}$-affinity chromatography. The second step was the cleavage of the tag by the tobacco etch virus (TEV) protease performed over night at 4° C. To separate the protein from the $His_6$-tag and the $His_6$-tagged TEV protease a second $Ni^{2+}$-affinity chromatography has been performed in the third step. Fourth and final step of the protein purification was size-exclusion chromatography on a HiLoad 16/600 Superdex 200 pg (GE Healthcare). The final protein solution was concentrated and stored with 50% glycerol at −20° C.

A Polymerase Activity Assay

This experiment compares the DNA polymerase activity of the PB polymerase with certain commercially available polymerases using a molecular beacon assay at 25° C.

The polymerase activity assay is based on a molecular beacon probe (modified from Summerer, *Methods Mol. Biol.*, 2008, 429, 225-235). The molecular beacon template consists of a 23 mer loop that is connected by a GC-rich 8 mer stem region (sequence is indicated in italics) and a 43 mer extension. Due to the loop formation the fluorophores Dabcyl and FAM are in close proximity and thus quenched. Upon extension by the DNA polymerase I of the primer that is annealed to the molecular beacon template the stem is opened and the increase in distance of the two fluorophores is measured by the restoration of FAM fluorescence (excitation 485 nm, emission 518 nm).

Molecular Beacon Template (SEQ ID NO: 9)
5'-*GGCCCGT*$^{Dabcyl}$AGGAGGAAAGGACATCTTCTAGCAT$^{FAM}$ACGGGCCG
TCAAGTTCATG GCCAGTCAAGTCGTCAGAAATTTCGCACCAC-3' primer
(SEQ ID NO: 10)
5'-GTGGTGCGAAATTTCTGAC-3'

The molecular beacon substrate was produced by incubating 20 µl of 10 µM molecular beacon template and 15 µM primer in 10 mM Tris-HCl pH 8.0, 100 mM NaCl for 5 min at 95° C. The reaction was then let to cool down at room temperature for 2 h. The substrate solution was stored at −20° C. with a final concentration of 10 µM.

Fifty microliter reactions consisted of 200 nM substrate and 200 µM dNTP (equimolar amounts of dATP, dGTP, dCTP and dTTP). For PB polymerase I the reaction further contained 5 mM $MgCl_2$ in 50 mM BIS-TRIS propane at pH 8.5, 100 mM NaCl, 1 mM DTT, 0.2 mg/ml BSA and 2% glycerol. For the commercially known polymerase Is the respective reaction buffer supplied by New England Biolabs has been used. Final salt concentration in the reaction buffer has been adjusted to 100 mM according to the optimal salt for the respective polymerases. The activity assay was carried out at 25° C. in black 96-well fluorescence assay plates (Corning®). The reaction was initiated by addition of protein solution (i.e. addition of polymerase). The increase in FAM fluorescence was measured as relative fluorescence units in appropriate time intervals by exciting at 485 nm and emission at 518 nm. The measurement was performed in a SpectraMax® Gemini Microplate Reader (Molecular Devices).

Figure 1:
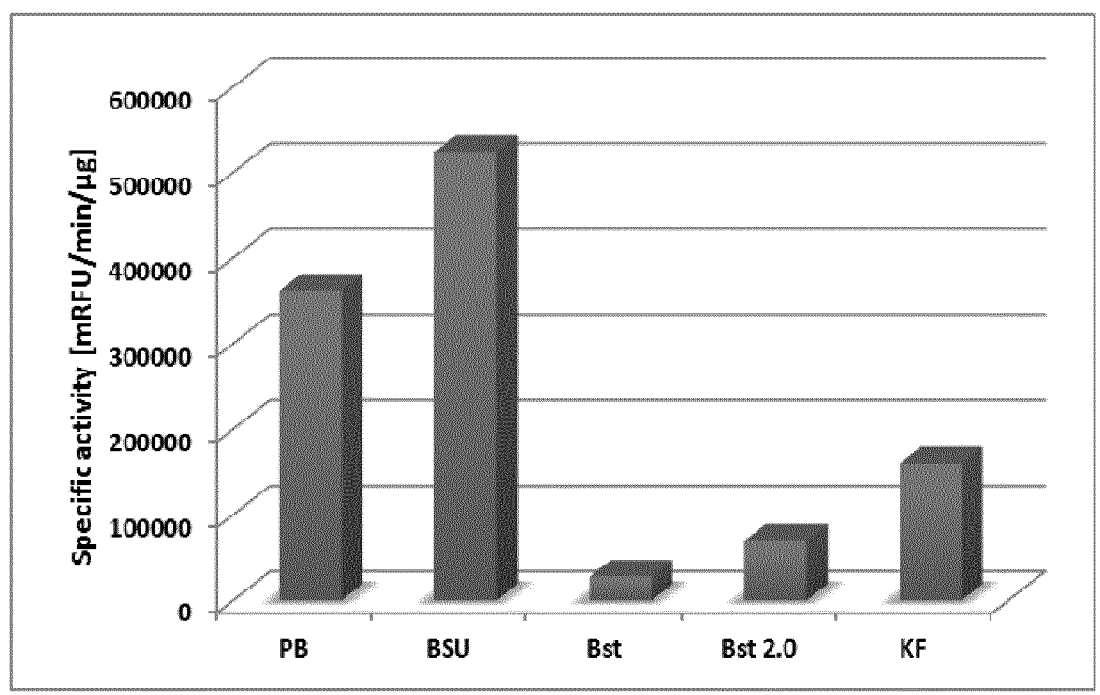

Results of this polymerase activity assay are shown in FIG. 1. The PB polymerase shows higher polymerase activity than the commercially (New England Biolabs) available polymerases KF (Klenow fragment *E. coli*), Bst (polymerase from *G. stearothermophilus*), Bst 2.0 (polymerase from *G. stearothermophilus*). Only the BSU polymerase from *B. subtilis* shows a higher polymerase activity at this temperature.

The same type of polymerase activity assay was also performed in order to compare the DNA polymerase activity of the PB polymerase with other DNA polymerases from marine sources (data not shown). The PB polymerase had a markedly higher polymerase activity compared with the other marine polymerases tested (e.g. *Aliivibrio salmonicida* DNA polymerase).

Strand-Displacement Activity Assay

This experiment compares the strand-displacement activity of the PB DNA polymerase with certain commercially available polymerases using a strand-displacement activity assay at 25° C. The ability of a polymerase to displace a strand, termed strand displacement, is important for many isothermal amplification methods.

Figure 2:
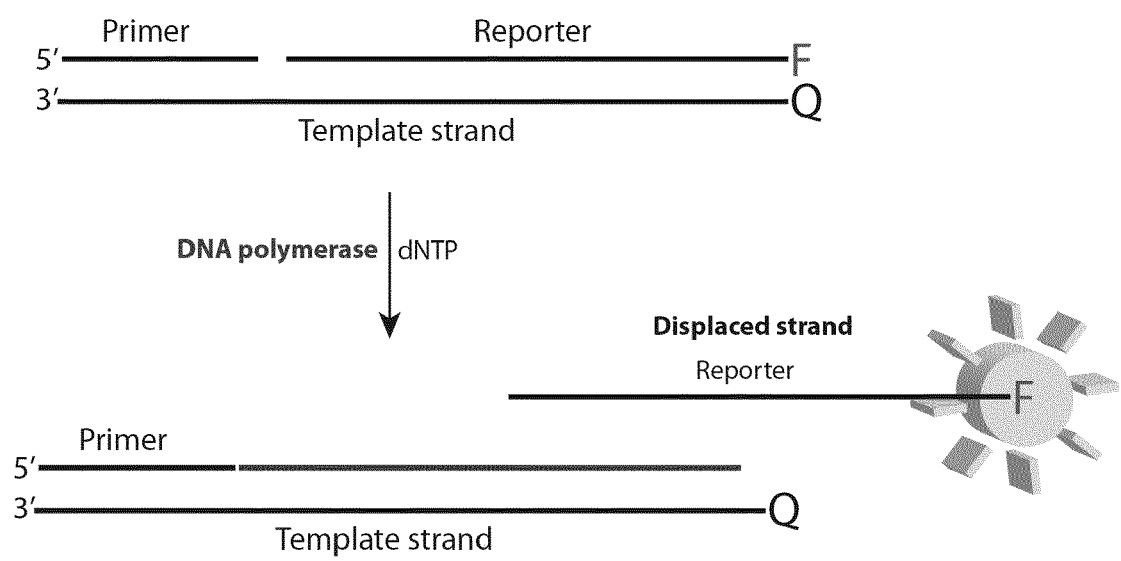

Important in assessing the strand-displacement property is the design a robust assay. An overview of the assay setup is shown in FIG. 2. The assay is based on an increase in fluorescence signal that is measured upon displacement of the quenched reporter strand which is only achievable through strand-displacement activity of the DNA polymerase. As control the strand-displacement negative polymerase T4 is used and showed no activity in the assay (result not shown).

The substrate for the strand-displacement activity assay consists of a "cold" primer of 19 oligonucleotides (SEQ ID NO:11) and a reporter strand consisting of 20 oligonucleotides that is labeled with the TAMRA fluorophore (F) at its 3' end (SEQ ID NO:12). The template strand consists of 40 oligonucleotides and is labeled with the Black Hole Quencher 2 (BHQ2) at its 5' end (SEQ ID NO:13). The primers are annealed to the template strand leaving a one nucleotide gap at position 20 on the template strand. Furthermore are the labels in close proximity and thus the fluorophore TAMRA is quenched by BHQ2. Upon strand-displacement activity of the DNA polymerase I the TAMRA labeled oligonucleotide is displaced from the template strand. As a consequence the fluorophore and the quencher are no longer in close proximity and an increase in TAMRA fluorescence can be measured (excitation 525 nm, emission 598 nm).

5'-TATCCACCAATACTACCCT CGATACTTTGTCCACTCAAT[TAMRA]-3'

3'-ATAGGTGGTTATGATGGGATGCTATGAAACAGGTGAGTTA[BHQ2]-5'

The strand-displacement activity of PB polymerase expressed as mRFU/min/µg has been analysed using the above-described strand-displacement activity assay. The substrate for the strand-displacement activity assay was produced by incubating 20 µl of 10 µM "cold" primer, 10 µM reporter strand and 10 µM template strand in 10 mM Tris-HCl pH 8.0, 100 mM NaCl at 95° C. for 5 min. The reaction was then let to cool down at room temperature for 2 h. The substrate solution was stored at −20° C. with a final concentration of 10 µM.

Fifty microliter reactions consisted of 200 nM substrate and 200 µM dNTP (equimolar amounts of dATP, dGTP, dCTP and dTTP). For PB polymerase I the reaction further contained 5 mM $MgCl_2$ in 50 mM BIS-TRIS propane at pH 8.5, 100 mM NaCl, 1 mM DTT, 0.2 mg/ml BSA and 2% glycerol. For the commercially known polymerase Is the respective reaction buffer supplied by New England Biolabs has been used. Final salt concentration in the reaction buffer has been adjusted to 100 mM according to the optimal salt for the respective polymerases. The activity assay was carried out at 25° C. in black 96-well fluorescence assay plates (Corning®). The reaction was initiated by addition of protein solution (i.e. addition of polymerase). The increase in TAMRA fluorescence was measured as relative fluorescence units in appropriate time intervals by exciting at 525 nm and recording emission at 598 nm. The measurement was performed in a SpectraMax® M2e Microplate Reader (Molecular Devices).

Figure 3:
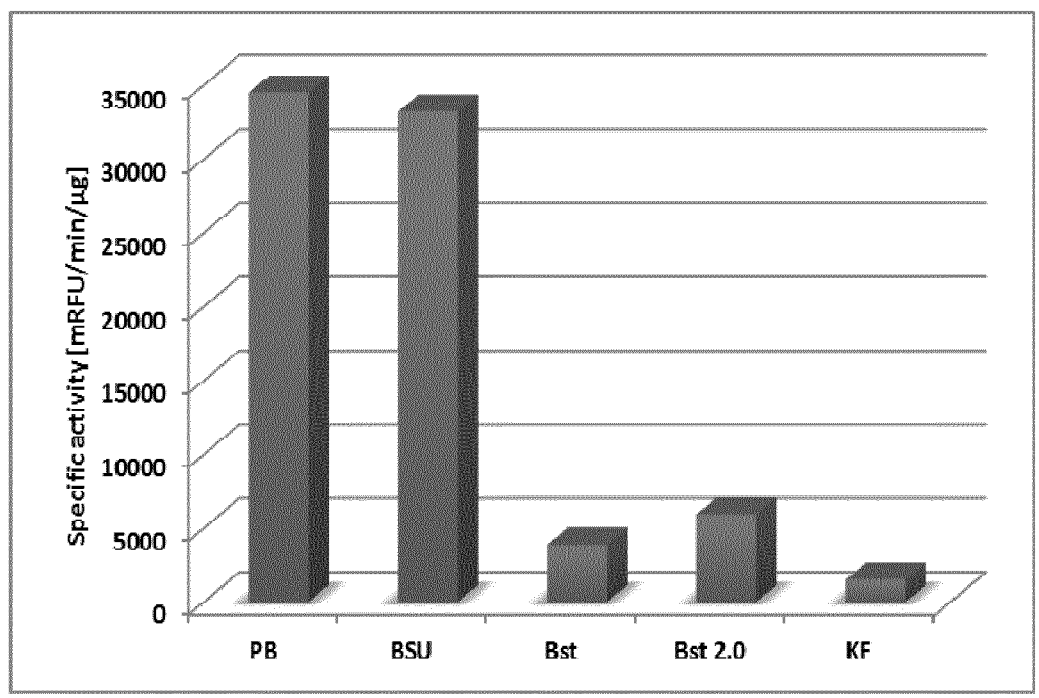
FIG. 3 shows a comparison of the strand-displacement activity at 25° C. (specific activity) of the recombinantly produced marine polymerase from *Psychrobacillus* sp. (PB) with other polymerases. The commercially known polymerases are KF (Klenow Fragment *E. coli*), Bst (*G. stearothermophilus*), Bst 2.0 (*G. stearothermophilus*) and BSU (*B. subtilis*).

Results of this strand-displacement activity assay are shown in FIG. 3. The results show that the polymerase from *Psychrobacillus* sp. (PB) possesses superior strand displacement activity than the commercially available polymerases KF (Klenow fragment *E. coli*), Bst (polymerase from *G. stearothermophilus*), Bst 2.0 (polymerase from *G. stearothermophilus*). The *Psychrobacillus* sp. (PB) DNA polymerase shows comparable strand displacement-activity to the commercially available BSU (*B. subtilis*) polymerase.

The same type of strand-displacement activity assay was also performed in order to compare the DNA polymerase activity of the PB polymerase with other DNA polymerases from marine sources (data not shown). The PB polymerase had a markedly higher strand-displacement activity compared with the other marine polymerases tested (e.g. *Aliivibrio salmonicida* DNA polymerase).

Analysis of Effect of Salt Concentration on Polymerase Activity

In crude samples, such as blood, there may be several compounds present that can inhibit the polymerase reaction. One such compound is salt (high salt content). An experiment to assess the effect of salt concentration on polymerase activity was performed as described below.

The optimum NaCl concentration for PB DNA polymerase has been analysed using the described polymerase activity assay varying the amount of salt present in the reaction buffer. One hundred percent activity refers to the salt concentration giving highest polymerase activity. Put another way, for each of the tested DNA polymerases the maximum polymerase activity observed is set as the 100% activity value. The other values (data points) in each curve are relative to the 100% activity for the respective polymerase.

Fifty microliter reactions consisted of 200 nM substrate and 200 µM dNTP (equimolar amounts of dATP, dGTP, dCTP and dTTP). For PB polymerase I the reaction further contained 5 mM $MgCl_2$ in 50 mM BIS-TRIS propane at pH 8.5, 1 mM DTT, 0.2 mg/ml BSA and 2% glycerol. The buffers for the commercially known polymerase Is have been prepared according to the composition of the respective buffer supplied by New England Biolabs omitting the salt. The respective NaCl concentrations tested in this experiment have been added to each reaction individually. The activity assay was carried out at 25° C. in black 96-well fluorescence assay plates (Corning®). The reaction was initiated by addition of protein solution with 1 µg/ml for PB, 16 units/ml for Bst, 16 units/ml for Bst 2.0, 2.5 units/ml for BSU or 2 units/ml for KF. The increase in FAM fluorescence was measured as relative fluorescence units in appropriate time intervals by exciting at 485 nm and emission at 518 nm. The measurement was performed in a SpectraMax® Gemini Microplate Reader (Molecular Devices).

Figure 4:
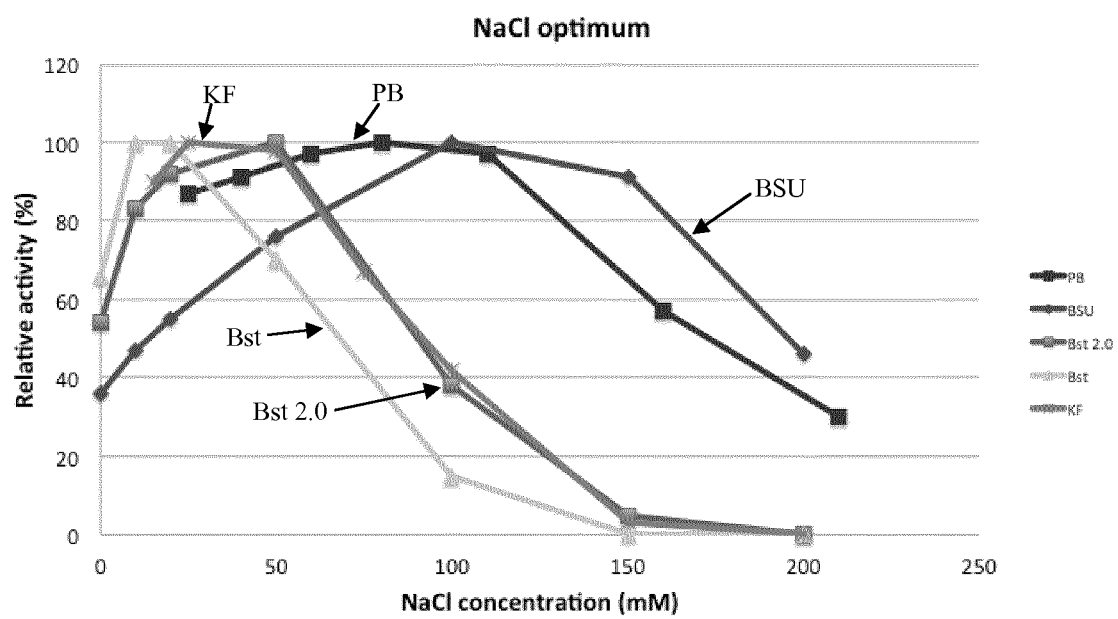
FIG. 4 shows the polymerase activity of the PB polymerase and other polymerases at various NaCl concentrations. The commercially known polymerases are KF (Klenow Fragment *E. coli*), Bst (*G. stearothermophilus*), Bst 2.0 (*G. stearothermophilus*) and BSU (*B. subtilis*).

The results of this experiment are shown in FIG. 4. As is evident from FIG. 4, the PB DNA polymerase exhibits tolerance to range of different salt concentrations.

Effect of Temperature on Polymerase Activity of PB Polymerase

The effect of temperature on the polymerase activity of PB polymerase I has been investigated with the single-nucleotide incorporation assay.

Single-Nucleotide Incorporation Assay

A primer consisting of 19 oligonucleotides (SEQ ID NO:15) is annealed to a template strand consisting of 40 oligonucleotides (SEQ ID NO:14). The primer is labeled with the FAM fluorophore at its 5' end. In the reaction set up only dATP will be provided thus the polymerase can extend the primer in 5'-3' direction only by one nucleotide at position 20. The subsequent analysis on a denaturing polyacrylamide gel (12% polyacrylamide/7 M urea) and scanning for the FAM labeled oligonucleotides shows the primer consisting of 19 oligonucleotides and the primer extended by the nucleotide adenine thus consisting of 20 oligonucleotides. Enzyme activity is determined by densitometric measurement of bands representing the extended primer (intensity 1) and the unextended primer (intensity 0). The relative incorporation rate is calculated as follows:

incorporation [%]=intensity 1/(intensity 0+intensity 1)*100

```
5'-ATTGAGTGGAGATAGTATCGTAGGGTAGTATTGGTGGATA-3'
40 mer

3'-TCCCATCATAACCACCTAT[FAM]-5' 19 mer
```

The substrate for the single-nucleotide incorporation assay was produced by incubating 20 µl of 0.5 µM fluorophore-labeled primer and 0.5 µM template DNA in 10 mM Tris-HCl pH 8.0, 100 mM NaCl at 75° C. for 5 min. The reaction was then let to cool down at room temperature for 2 h. The substrate solution was stored at −20° C. with a final concentration of 0.5 µM.

Ten microliter reactions contained 30 nM substrate and 10 µM dATP. For PB polymerase I the reaction further contained 5 mM $MgCl_2$ in 50 mM Tris at pH 8.5, 100 mM NaCl, 1 mM DTT, 0.2 mg/ml BSA and 2% glycerol. The pH of the reaction buffer at room temperature was adjusted to be pH 8.5 at the respective incubation temperature. The reactions were initiated by addition of 0.018 ng/µl protein PB polymerase I and incubated for 15 min at the respective temperature (i.e. the temperatures corresponding to the data points on FIG. 5). As a negative control protein dilution buffer has been used instead of protein solution.

Reactions were stopped by addition of 2.5 µl denaturing gel loading buffer (95% formamide, 10 mM EDTA, 0.1% xylene cyanol) and incubation at 95° C. for 5 minutes. For the denaturing polyacrylamide gel electrophoresis (12% polyacrylamide/7 M urea) a sample volume of 6 µl was loaded onto the gel. The gel electrophoresis was performed in 0.5×TBE buffer (44.5 mM Tris, 44.5 mM boric acid, 1 mM EDTA) at 50 W for 1 hour 15 minutes and the gel subsequently scanned with the PharosFX Plus Imager (Bio-Rad).

Figure 5:
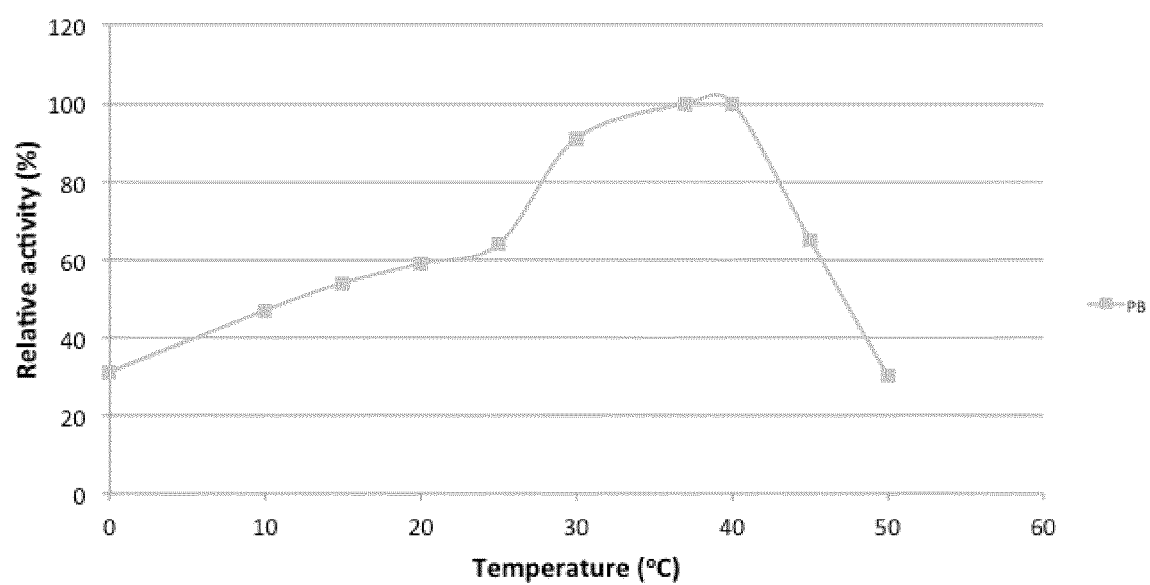
FIG. 5 shows the effect of temperature on polymerase activity of PB polymerase.

Results of this experiment are shown in FIG. 5. One hundred percent activity refers to the temperature value with the highest activity. Put another way, for the tested PB DNA polymerase the maximum polymerase activity observed is set as the 100% activity value. The other values (data points) in each curve are relative to the 100% activity for the respective polymerase. By way of an example, at an incubation temperature of 20° C., the polymerase activity of the PB polymerase is about 60% of the maximum PB polymerase activity observed, i.e. there is about 60% "relative" activity.

The results in FIG. 5 show that the PB polymerase has significant polymerase activity across a broad range of temperatures.

Effect of Temperature on the Stability of PB Polymerase Compared to KF (Klenow Fragment).

The effect of temperature on the stability of PB polymerase I has been investigated with the single-nucleotide incorporation assay.

Single-Nucleotide Incorporation Assay

A primer consisting of 19 oligonucleotides (SEQ ID NO:15) is annealed to a template strand consisting of 40 oligonucleotides (SEQ ID NO:14). The primer is labeled with the FAM fluorophore at its 5' end. In the reaction set up only dATP will be provided thus the polymerase can extend the primer in 5'-3' direction only by one nucleotide at position 20. The subsequent analysis on a denaturing polyacrylamide gel (12% polyacrylamide/7 M urea) and scanning for the FAM labeled oligonucleotides shows the primer consisting of 19 oligonucleotides and the primer extended by the nucleotide adenine thus consisting of 20 oligonucleotides. Enzyme activity is determined by densitometric measurement of bands representing the extended primer (intensity 1) and the unextended primer (intensity 0). The relative incorporation rate is calculated as follows:

incorporation [%]=intensity 1/(intensity 0+intensity 1)*100

```
5'-ATTGAGTGGAGATAGTATCGTAGGGTAGTATTGGTGGATA-3'
40 mer

3'-TCCCATCATAACCACCTAT[FAM]-5' 19 mer
```

The substrate for the single-nucleotide incorporation assay was produced by incubating 20 µl of 0.5 µM fluorophore-labeled primer and 0.5 µM template DNA in 10 mM Tris-HCl pH 8.0, 100 mM NaCl at 75° C. for 5 min. The reaction was then let to cool down at room temperature for 2 h. The substrate solution was stored at −20° C. with a final concentration of 0.5 µM.

For PB polymerase 110 µl reactions were performed in 50 mM BIS-TRIS propane at pH 8.5, 100 mM NaCl, 5 mM $MgCl_2$, 1 mM DTT, 0.2 mg/ml BSA and 2% glycerol. To test the inactivation temperature 0.018 ng/µl of PB polymerase I were added to the reaction buffer, incubated at the respective temperature (i.e. the temperatures corresponding to the data points on FIG. 6) for 15 min and afterwards cooled down on ice for 5 min. For KF the reaction buffer has been prepared according to the composition of the respective buffer supplied by New England Biolabs with optimal pH at 25° C. The protein has been added to the reaction buffer with 0.67 units/ml and the reactions have been incubated as described for the PB polymerase I. As a negative control protein dilution buffer has been used instead of protein solution.

The single-nucleotide extension reaction was initiated by addition of 30 nM substrate and 10 µM dATP and the mixture was incubated at 25° C. for 15 min. The reaction was stopped by addition of 2.5 µl denaturing gel loading buffer (95% formamide, 10 mM EDTA, 0.1% xylene cyanol) and incubation at 95° C. for 5 minutes. For the denaturing polyacrylamide gel electrophoresis (12% polyacrylamide/7 M urea) a sample volume of 6 µl was loaded onto the gel. The gel electrophoresis was performed in 0.5×TBE buffer (44.5 mM Tris, 44.5 mM boric acid, 1 mM EDTA) at 50 W for 1 hour 15 minutes and the gel subsequently scanned with the PharosFX Plus Imager (Bio-Rad).

Figure 6:
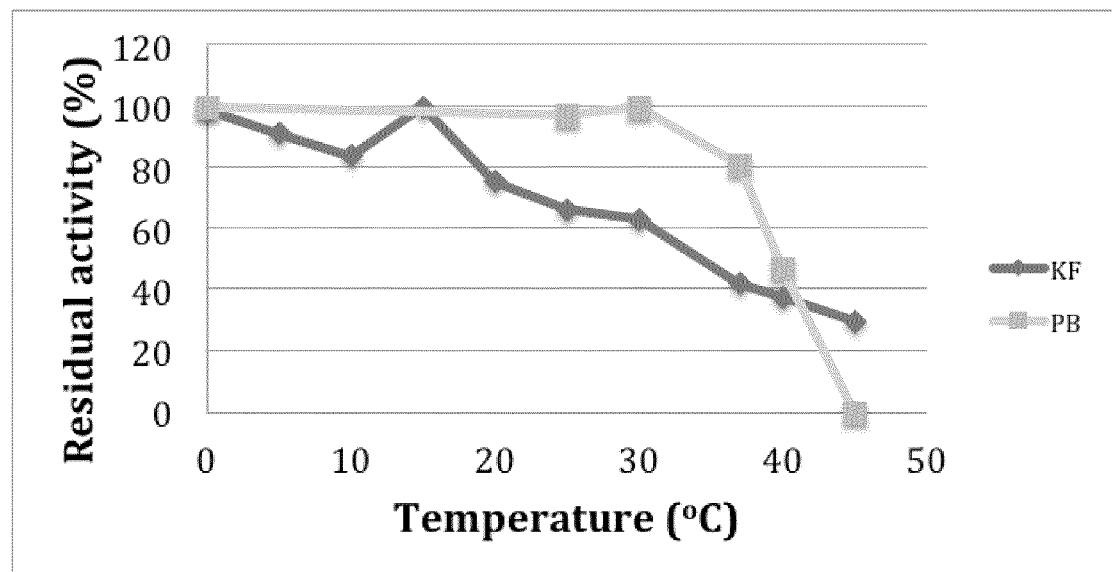
FIG. 6 shows the effect of temperature on the stability of the PB polymerase compared to KF. KF is Klenow Fragment (*E. coli*).

Results of this experiment are shown in FIG. 6. One hundred percent activity refers to enzyme sample incubated on ice (0° C.). Put another way, for each of the tested DNA polymerases (PB and Klenow Fragment from *E. coli* (KF)) the polymerase activity observed when the polymerase was incubated on ice (0° C.) for 15 minutes prior to the initiation of the single-nucleotide extension reaction is set as the 100% activity value. The other values (data points) in each curve are relative to the 100% activity for the respective polymerase. By way of an example, after a 15 minute incubation at 37° C. prior to the initiation of the single-nucleotide extension reaction, the polymerase activity of the PB polymerase is about 80% of the PB polymerase activity observed when the 15 minute incubation prior to the initiation of the single-nucleotide extension reaction was done on ice (0° C.), i.e. there is about 80% "residual" activity.

The results in FIG. 6 show that in comparison with KF, the PB polymerase retains higher polymerase activity after prior incubations at a range of temperatures. Put another way, the PB polymerase is more temperature stable than the KF polymerase. For example, with an incubation at 30° C. for 15 minutes prior to the initiation of the single-nucleotide extension reaction, the PB polymerase retains the same polymerase activity as when the incubation prior to the initiation of the single-nucleotide extension reaction was done on ice (0° C.) (i.e. there is 100% residual activity with a 30° C. incubation). In contrast, with an incubation at 30° C. for 15 minutes prior to the initiation of the single-nucleotide extension reaction, the KF polymerase has only about 60% of the polymerase activity observed when the incubation prior to the initiation of the single-nucleotide extension reaction was done on ice (0° C.) (i.e. there is about 60% residual activity with a 30° C. incubation).

The same type of assay was also performed in order to compare the DNA polymerase activity of the PB polymerase with other DNA polymerases from marine sources (data not shown). The PB polymerase had a markedly higher stability compared with the other marine polymerases tested (e.g. *Aliivibrio salmonicida* DNA polymerase).

Biophysical Data Showing the Melting Temperature of PB Polymerase in Different pH Buffers The melting temperature ($T_m$) of the protein was determined by thermofluor experiments according to Ericsson et al. (*Anal. Biochem.*, 2006, 357, 289-298). A number of buffers of pH 6.0 to pH 9.5 in the concentration of 50 mM have been tested. The respective buffer, SYPRO® Orange (Sigma Aldrich) in a final dilution of 6× and 12.5 µg of protein (i.e. PB polymerase) were mixed thoroughly in a well of a thin-wall PCR plate (Biorad). The wells were sealed with optical-quality sealing tape (Biorad). The volume of the final reaction was 25 µl. A temperature range of 10-90° C. with an increment of 0.3° C. at 3 seconds intervals has been scanned in the thermofluor experiment.

Figure 7:
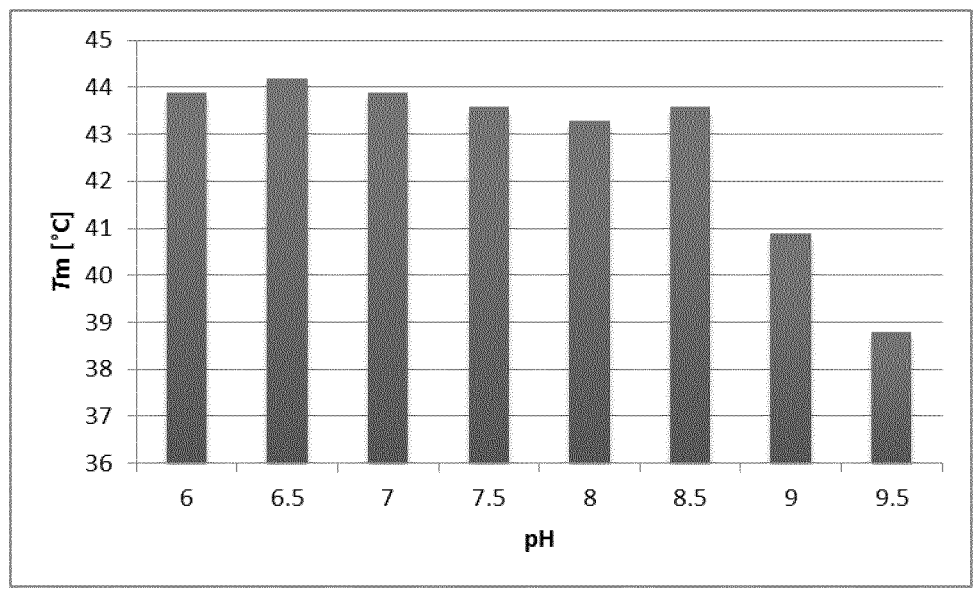
FIG. 7 shows the melting temperature ($T_m$ (° C.)) analysis of the PB polymerase I at different pH.

Results of this experiment are shown in FIG. 7. PB polymerase I shows a broad pH stability profile at the range of pH 6-8.5 with a melting temperature averaging about 43-44° C. further proving its relative broad temperature application range.

Processivity

Processivity is the ability of the DNA polymerase to remain bound to the DNA template strand during synthesis (nucleotide incorporation) before dissociating, and the overall efficiency of DNA synthesis may therefore increase with increasing processivity of a given polymerase. This feature may be important especially if longer stretches of DNA needs to be synthesized. The processivity assay is therefore designed to measure the extent of polymerization after a single binding event. In order for the extension products to reflect the processivity of the polymerase, an excess of trap DNA was added in this case to ensure that each primer template is extended only once.

```
100-mer template
                                        (SEQ ID NO: 16)
3'ATGTTGGTTCTCGTATGCTGCCGGTCACGGCTTAAGTGTGCCACAAC
ACACAACCAACACCACCACAACACACCAACAACCACAACACACACAACC
ACAC-5'

Fam labeled 20-mer primer
                                        (SEQ ID NO: 17)
5'FAM-TACAACCAAGAGCATACGAC
```

To prepare a primer-template DNA substrate, a 100 mer template (0.5 µM) was incubated with a 20 mer FAM labeled primer (0.5 µM) in the presence of 50 mM NaCl and 50 mM tris/HCl pH 7.5 for 5 minutes at 75° C., and left to cool down to room temperature for at least 2 hours. The PB polymerase I and the commercial polymerases (New England Biolabs) tested herein were pre-incubated with the DNA substrate (25 nM) and dNTPs (10 µM) in 50 mM Tris-HCl (pH 8.5 for PB polymerase I and T7 DNA polymerase, pH 7.5 for Bst 2.0 and BSU), 50 mM KCl (PB polymerase I, Bst 2.0, T7 DNA polymerase) or 50 mM NaCl (BSU), 0.2 mg/ml BSA, 1 mM DTT and 2% glycerol for 10 min at 25° C.

The reaction (Pr) was initiated by adding 5 mM $MgCl_2$ and 1.1 mg/ml Herring sperm DNA as a trap and terminated after 2 minutes by adding stop solution (95% formamide 10 mM EDTA, 0.05% bromophenol blue). To show the effectiveness of the trap, the same amount of Pbl was pre incubated with 1.1 mg/ml trap and the DNA substrate before initiation of the reaction with $MgCl_2$ (R0) in a parallel reaction. As a control for complete polymerization of the primed substrate, another reaction (P) was run without adding any trap, under the same reaction conditions. Amount of enzymes that provided equivalent polymerase activity in the P reaction was used as a starting point for processivity analysis. Thus, the following amounts of enzymes for processivity analysis were used: PB polymerase I 0.013 µg, Bst 2.0 0.14 µg and BSU 0.016 µg.

The reactions were heated for 5 minutes at 95° C. and the products were resolved on 10% TBE-polyacrylamide gel containing 8 M Urea. The image was then visualized by Pharose FX Plus imager (BioRad).

Results of this experiment are shown in FIG. 8. These results show that PB polymerase has a significantly higher processivity compared to Bsu and Bst2.0, where they perform in order PB>Bsu>Bst 2.0.

The invention claimed is:

1. An isolated DNA polymerase, said DNA polymerase comprising the amino acid sequence of SEQ ID NO:1 or comprising an amino acid sequence which is at least 90% identical to SEQ ID NO:1, wherein said DNA polymerase lacks a 5'-3' exonuclease domain.

2. The isolated DNA polymerase according to claim 1, wherein said DNA polymerase comprises the amino acid sequence of SEQ ID NO:1.

3. The isolated DNA polymerase according to claim 1, wherein said DNA polymerase exhibits at least 30% of its maximum polymerase activity across the temperature range from 0° C. to 35° C.

4. The isolated DNA polymerase according to claim 1, wherein said DNA polymerase exhibits at least 60% of its maximum polymerase activity across the temperature range from 20° C. to 35° C.

5. The isolated DNA polymerase according to claim 1, wherein at a temperature that deviates by up to about 10° C. from the temperature at which said DNA polymerase exhibits maximum activity, said DNA polymerase exhibits at least 30% of its maximum polymerase activity.

6. The isolated DNA polymerase according to claim 1, wherein said DNA polymerase exhibits at least 40% of its maximum activity after incubation for 15 minutes of said DNA polymerase at any temperature across the temperature range from 0° C. to 40° C. prior to assessing DNA polymerase activity.

7. The isolated DNA polymerase according to claim 1, wherein said DNA polymerase exhibits at least 60% of its maximum activity after incubation for 15 minutes of said DNA polymerase at any temperature across the temperature range from 0° C. to 37° C. prior to assessing DNA polymerase activity.

8. The isolated DNA polymerase according to claim 1, wherein said DNA polymerase has a melting temperature of about 42° C.-45° C. in the pH range 6.0 to 8.5.

9. The isolated DNA polymerase according to claim 1, wherein said DNA polymerase has a higher polymerase activity than the *E.coli* Klenow fragment DNA polymerase, the *Geobacillus stearothermophilus* DNA polymerase and/or DNA polymerase from *Aliivibrio Salmonicida*, wherein said DNA polymerase activity is as assessed at about 25° C.

10. The isolated DNA polymerase according to claim 1, wherein said DNA polymerase has at least 50% higher strand displacement activity than the *E.coli* Klenow fragment DNA polymerase, the *Geobacillus stearothermophilus* DNA polymerase and/or the DNA polymerase from *Aliivibrio Salmonicida*.

11. The isolated DNA polymerase according to claim 1, wherein said DNA polymerase has higher processivity than the *Bacillus subtilis* DNA polymerase.

12. The isolated DNA polymerase according to claim 1, wherein across a concentration range from 0mM to 210mM NaCl, said DNA polymerase exhibits at least 30% of its maximum polymerase activity.

13. A composition comprising a DNA polymerase according to claim 1 and a buffer.

14. A method of nucleotide polymerisation using a DNA polymerase according to claim 1, said method comprising the steps of:
 (i) providing a reaction mixture comprising said DNA polymerase, a template nucleic acid molecule, an oligonucleotide primer which is capable of annealing to a portion of the template nucleic acid molecule and one or more species of nucleotide; and
 (ii) incubating said reaction mixture under conditions whereby the oligonucleotide primer anneals to the template nucleic acid molecule and said DNA polymerase extends said oligonucleotide primer by polymerising one or more nucleotides.

15. A method of amplifying a nucleic acid using a DNA polymerase according to claim 1, said method comprising the steps of:
 (i) providing a reaction mixture comprising said DNA polymerase, a template nucleic acid molecule, an oligonucleotide primer(s) which is capable of annealing to a portion of the template nucleic acid molecule acid molecule, and nucleotides;
 (ii) incubating said reaction mixture under conditions whereby the oligonucleotide primer(s) anneals to the template nucleic acid molecule and said DNA polymerase extends said oligonucleotide primer(s) by polymerising one or more nucleotides to generate a polynucleotide.

16. The method of claim 14, wherein said method is performed at a constant temperature.

17. The method of claim 16, wherein said constant temperature is 0° C. to 42° C.

18. The method of 17, wherein said constant temperature is 10° C. to 25° C.

19. The method of claim 15, wherein said method is performed at a constant temperature.

20. The method of claim 19, wherein said constant temperature is 0° C. to 42° C.

21. The method of 20, wherein said constant temperature is 10° C. to 25° C.

22. The isolated DNA polymerase of claim 1, wherein said DNA polymerase comprises an amino acid sequence that is at least 95% identical to SEQ ID NO:1.

* * * * *

SEQUENCE LISTING

```
<160> NUMBER OF SEQ ID NOS: 17

<210> SEQ ID NO 1
<211> LENGTH: 580
<212> TYPE: PRT
<213> ORGANISM: Artificial Sequence
<220> FEATURE:
<223> OTHER INFORMATION: Truncated PB polymerase

<400> SEQUENCE: 1

Thr Glu Val Ala Phe Glu Ile Val Glu Glu Ile Asp Ser Thr Ile Leu
1               5                   10                  15

Asp Lys Val Met Ser Val His Leu Glu Met Tyr Asp Gly Gln Tyr His
            20                  25                  30

Thr Ser Glu Leu Leu Gly Ile Ala Leu Ser Asp Gly Glu Lys Gly Tyr
        35                  40                  45

Phe Ala Pro Ala Asp Ile Ala Phe Gln Ser Lys Asp Phe Cys Ser Trp
    50                  55                  60

Leu Glu Asn Ala Thr Asn Lys Lys Tyr Leu Ala Asp Ser Lys Ala Thr
65                  70                  75                  80

Gln Ala Val Ser Arg Lys His Asn Val Asn Val His Gly Val Glu Phe
                85                  90                  95

Asp Leu Leu Leu Ala Ala Tyr Ile Val Asn Pro Ala Ile Ser Ser Glu
            100                 105                 110

Asp Val Ala Ala Ile Ala Lys Glu Phe Gly Tyr Phe Asn Leu Leu Thr
        115                 120                 125

Asn Asp Ser Val Tyr Gly Lys Gly Ala Lys Lys Thr Ala Pro Glu Ile
    130                 135                 140

Glu Lys Ile Ala Glu His Ala Val Arg Lys Ala Arg Ala Ile Trp Asp
145                 150                 155                 160

Leu Lys Glu Lys Leu Glu Val Lys Leu Glu Glu Asn Glu Gln Tyr Ala
                165                 170                 175

Leu Tyr Lys Glu Ile Glu Leu Pro Leu Ala Ser Ile Leu Gly Thr Met
            180                 185                 190

Glu Ser Asp Gly Val Leu Val Asp Lys Gln Ile Leu Val Glu Met Gly
        195                 200                 205

His Glu Leu Asn Ile Lys Leu Arg Ala Ile Glu Gln Asp Ile Tyr Ala
    210                 215                 220

Leu Ala Gly Glu Thr Phe Asn Ile Asn Ser Pro Lys Gln Leu Gly Val
225                 230                 235                 240

Ile Leu Phe Glu Lys Ile Gly Leu Thr Pro Ile Lys Lys Thr Lys Thr
                245                 250                 255

Gly Tyr Ser Thr Ala Ala Asp Val Leu Glu Lys Leu Ala Ser Glu His
            260                 265                 270

Glu Ile Ile Glu Gln Ile Leu Tyr Arg Gln Leu Gly Lys Leu Asn
        275                 280                 285

Ser Thr Tyr Ile Glu Gly Leu Leu Lys Glu Ile His Glu Asp Asp Gly
    290                 295                 300

Lys Ile His Thr Arg Tyr Gln Gln Ala Leu Thr Ser Thr Gly Arg Leu
305                 310                 315                 320
```

```
Ser Ser Ile Asn Pro Asn Leu Gln Asn Ile Pro Val Arg Leu Glu Glu
            325                 330                 335

Gly Arg Lys Ile Arg Lys Ala Phe Val Pro Ser Gln Pro Gly Trp Val
        340                 345                 350

Met Phe Ala Ala Asp Tyr Ser Gln Ile Glu Leu Arg Val Leu Ala His
        355                 360                 365

Met Ser Glu Asp Glu Asn Leu Val Glu Ala Phe Asn Asn Asp Leu Asp
    370                 375                 380

Ile His Thr Lys Thr Ala Met Asp Val Phe His Val Glu Gln Glu Ala
385                 390                 395                 400

Val Thr Ser Asp Met Arg Arg Ala Ala Lys Ala Val Asn Phe Gly Ile
                405                 410                 415

Val Tyr Gly Ile Ser Asp Tyr Gly Leu Ser Gln Asn Leu Asp Ile Thr
            420                 425                 430

Arg Lys Glu Ala Ala Thr Phe Ile Glu Asn Tyr Leu Asn Ser Phe Pro
        435                 440                 445

Gly Val Lys Gly Tyr Met Asp Asp Ile Val Gln Asp Ala Lys Gln Thr
    450                 455                 460

Gly Tyr Val Thr Thr Ile Leu Asn Arg Arg Arg Tyr Leu Pro Glu Ile
465                 470                 475                 480

Thr Ser Ser Asn Phe Asn Leu Arg Ser Phe Ala Glu Arg Thr Ala Met
                485                 490                 495

Asn Thr Pro Ile Gln Gly Ser Ala Ala Asp Ile Ile Lys Lys Ala Met
            500                 505                 510

Ile Asp Met Ala Glu Arg Leu Ile Ser Glu Asn Met Gln Thr Lys Met
        515                 520                 525

Leu Leu Gln Val His Asp Glu Leu Ile Phe Glu Ala Pro Pro Glu Glu
    530                 535                 540

Ile Ala Met Leu Glu Lys Ile Val Pro Glu Val Met Glu Asn Ala Ile
545                 550                 555                 560

Lys Leu Ile Val Pro Leu Lys Val Asp Tyr Ala Phe Gly Ser Ser Trp
                565                 570                 575

Tyr Asp Thr Lys
            580

<210> SEQ ID NO 2
<211> LENGTH: 1743
<212> TYPE: DNA
<213> ORGANISM: Artificial Sequence
<220> FEATURE:
<223> OTHER INFORMATION: Truncated PB polymerase

<400> SEQUENCE: 2
acagaagtag cattcgagat tgttgaagaa attgactcta caatattaga taaagtaatg      60
tcagtccatt tagaaatgta tgatgggcaa tatcatacaa gcgaattatt aggtattgct     120
ttatcagatg gagaaaaggg ttattttgct cctgctgata tagcttttca atcgaaggat     180
ttttgttctt ggttagaaaa tgctacgaat aaaagtatt tagcagactc caaagcaaca     240
caagcagtga gtagaaaaca taatgtgaat gtacatggag tggaattcga ccttcttta    300 gcagcgtata tagtaaatcc tgctatctct tcagaggatg ttgctgctat tgctaaagaa     360
tttggatatt ttaacttgct gacaaacgat agtgtttatg ggaaaggtgc aaaaaaacc    420 gcacctgaaa tcgagaaaat tgcagaacat gccgtaagaa aagcagggc tatttgggac    480 ttgaaagaaa agttagaagt aaaactggaa gaaaatgaac aatatgcgtt gtataaagaa    540
```

-continued

```
atagagctac cgcttgcatc tatccttggt acgatggaat cagatggggt gctggtggat    600
aaacaaattc ttgtagaaat gggtcatgag cttaatatta agttacgagc gattgaacaa    660
gacatttatg cgttagctgg tgaaacgttt aatattaatt cacctaaaca attaggtgta    720
atactatttg aaaaaattgg tcttacccct attaaaaaga caaaaacggg ctattcaact    780
gcagcagatg ttttggaaaa actagcaagt gaacatgaaa taatagagca aattttacta    840
tatcgtcaat taggtaaact caattccaca tatatcgaag gattattaaa agagattcat    900
gaagatgatg ggaagatcca tacccgatat caacaagccc taacttcaac tgggcgtttg    960
agttcgatca atccaaacct tcaaaatata ccagttcgtt tagaagaagg tagaaaaata   1020
cgtaaagcct ttgttccttc acaaccggga tgggtaatgt ttgcggcgga ttactctcaa   1080
attgaattgc gtgttcttgc ccatatgtct gaggatgaaa acctggtaga agcttttaat   1140
aatgatctgg atattcatac taaaacggct atggatgtat ccatgtgga gcaggaagca    1200
gtaacgtccg atatgcgccg tgctgctaag gcagttaact tgggattgt gtatggtatt    1260
agtgattatg gtttatcaca aaacctagat attactagaa agaagcggc gacatttatc    1320
gagaattatt taaatagctt cccaggtgta aaaggatata tggatgatat cgttcaagat   1380
gcgaaacaaa caggctacgt tacaacaatt ttgaatagac gaagatattt gcctgaaata   1440
acaagttcta actttaatct ccgcagtttt gcagaacgta ctgctatgaa tacaccaatt   1500
caagggagtg cagccgatat tattaaaaaa gcaatgatcg atatggcgga agattaata    1560
tcagaaaata tgcagaccaa aatgctacta caagtacatg atgaattaat ttttgaggct   1620
ccaccagagg aaattgcaat gctagaaaaa atagtgccag aggtgatgga aaacgctatt   1680
aaactgattg tacctttgaa agtggattat gcctttggtt catcttggta tgacacgaag   1740
tag                                                                 1743
```

<210> SEQ ID NO 3
<211> LENGTH: 877
<212> TYPE: PRT
<213> ORGANISM: Psychrobacillus sp.

<400> SEQUENCE: 3

```
Met Tyr Leu Ser Thr Glu Lys Ile Leu Leu Asp Gly Asn Ser Leu
 1               5                  10                  15

Ala Tyr Arg Ala Phe Phe Ala Leu Pro Leu Leu Thr Asn Glu His Gly
            20                  25                  30

Ile His Thr Asn Ala Val Tyr Gly Phe Thr Met Met Leu Gln Lys Ile
        35                  40                  45

Met Asp Glu Glu Asn Pro Thr His Met Leu Val Ala Phe Asp Ala Gly
    50                  55                  60

Lys Thr Thr Phe Arg His Ser Thr Phe Gly Asp Tyr Lys Gly Gly Arg
65                  70                  75                  80

Gln Lys Thr Pro Pro Glu Leu Ser Glu Gln Phe Pro Tyr Ile Arg Lys
                85                  90                  95

Leu Ile Asp Ala Tyr Gly Ile Lys Arg Tyr Glu Leu Glu Met Tyr Glu
            100                 105                 110

Ala Asp Asp Ile Ile Gly Thr Leu Ser Lys Arg Ala Asp Glu Lys Gly
        115                 120                 125

Gln Gln Val Val Ile Val Ser Gly Asp Lys Asp Leu Thr Gln Leu Ala
    130                 135                 140

Thr Asp Lys Thr Thr Val Tyr Ile Thr Arg Lys Gly Ile Thr Asp Ile
145                 150                 155                 160
```

```
Glu Lys Tyr Thr Pro Glu His Val Gln Glu Lys Tyr Gly Leu Thr Pro
                165                 170                 175
Leu Gln Ile Ile Asp Met Lys Gly Leu Met Gly Asp Ala Ser Asp Asn
            180                 185                 190
Ile Pro Gly Val Pro Gly Val Gly Glu Lys Thr Ala Ile Lys Leu Leu
        195                 200                 205
Lys Glu His Gly Ser Val Glu Asp Leu Tyr Lys Ala Leu Asp Thr Val
    210                 215                 220
Ser Gly Val Lys Leu Lys Glu Lys Leu Ile Ala Asn Glu Glu Gln Ala
225                 230                 235                 240
Ile Met Ser Lys Ala Leu Ala Thr Ile Glu Thr Ala Ala Pro Ile Gln
                245                 250                 255
Ile Ser Ile Asp Asp Leu Ser Tyr Thr Gly Pro Asn Met Glu Glu Val
            260                 265                 270
Ile Glu Val Trp Lys Glu Leu Ala Phe Lys Thr Leu Leu Glu Lys Ser
        275                 280                 285
Asp Tyr Ile Ser Glu Glu Ser Glu Thr Thr Glu Val Ala Phe Glu Ile
    290                 295                 300
Val Glu Glu Ile Asp Ser Thr Ile Leu Asp Lys Val Met Ser Val His
305                 310                 315                 320
Leu Glu Met Tyr Asp Gly Gln Tyr His Thr Ser Glu Leu Leu Gly Ile
                325                 330                 335
Ala Leu Ser Asp Gly Lys Gly Tyr Phe Ala Pro Ala Asp Ile Ala
            340                 345                 350
Phe Gln Ser Lys Asp Phe Cys Ser Trp Leu Glu Asn Ala Thr Asn Lys
        355                 360                 365
Lys Tyr Leu Ala Asp Ser Lys Ala Thr Gln Ala Val Ser Arg Lys His
    370                 375                 380
Asn Val Asn Val His Gly Val Glu Phe Asp Leu Leu Leu Ala Ala Tyr
385                 390                 395                 400
Ile Val Asn Pro Ala Ile Ser Ser Glu Asp Val Ala Ala Ile Ala Lys
                405                 410                 415
Glu Phe Gly Tyr Phe Asn Leu Leu Thr Asn Asp Ser Val Tyr Gly Lys
            420                 425                 430
Gly Ala Lys Lys Thr Ala Pro Glu Ile Glu Lys Ile Ala Glu His Ala
        435                 440                 445
Val Arg Lys Ala Arg Ala Ile Trp Asp Leu Lys Glu Lys Leu Glu Val
    450                 455                 460
Lys Leu Glu Glu Asn Glu Gln Tyr Ala Leu Tyr Lys Glu Ile Glu Leu
465                 470                 475                 480
Pro Leu Ala Ser Ile Leu Gly Thr Met Glu Ser Asp Gly Val Leu Val
                485                 490                 495
Asp Lys Gln Ile Leu Val Glu Met Gly His Glu Leu Asn Ile Lys Leu
            500                 505                 510
Arg Ala Ile Glu Gln Asp Ile Tyr Ala Leu Ala Gly Glu Thr Phe Asn
        515                 520                 525
Ile Asn Ser Pro Lys Gln Leu Gly Val Ile Leu Phe Glu Lys Ile Gly
    530                 535                 540
Leu Thr Pro Ile Lys Lys Thr Lys Thr Gly Tyr Ser Thr Ala Ala Asp
545                 550                 555                 560
Val Leu Glu Lys Leu Ala Ser Glu His Glu Ile Ile Glu Gln Ile Leu
                565                 570                 575
```

| | | | | | | | | | | | | |
|---|---|---|---|---|---|---|---|---|---|---|---|---|
|Leu|Tyr|Arg|Gln|Leu|Gly|Lys|Leu|Asn|Ser|Thr|Tyr|Ile|Glu|Gly|Leu|
| | |580| | | |585| | | |590| | | | | |
|Leu|Lys|Glu|Ile|His|Glu|Asp|Asp|Gly|Lys|Ile|His|Thr|Arg|Tyr|Gln|
| | |595| | | |600| | | |605| | | | | |

Leu Tyr Arg Gln Leu Gly Lys Leu Asn Ser Thr Tyr Ile Glu Gly Leu
            580                 585                 590

Leu Lys Glu Ile His Glu Asp Asp Gly Lys Ile His Thr Arg Tyr Gln
            595                 600                 605

Gln Ala Leu Thr Ser Thr Gly Arg Leu Ser Ser Ile Asn Pro Asn Leu
610                 615                 620

Gln Asn Ile Pro Val Arg Leu Glu Glu Gly Arg Lys Ile Arg Lys Ala
625                 630                 635                 640

Phe Val Pro Ser Gln Pro Gly Trp Val Met Phe Ala Ala Asp Tyr Ser
            645                 650                 655

Gln Ile Glu Leu Arg Val Leu Ala His Met Ser Glu Asp Glu Asn Leu
            660                 665                 670

Val Glu Ala Phe Asn Asn Asp Leu Asp Ile His Thr Lys Thr Ala Met
            675                 680                 685

Asp Val Phe His Val Glu Gln Glu Ala Val Thr Ser Asp Met Arg Arg
            690                 695                 700

Ala Ala Lys Ala Val Asn Phe Gly Ile Val Tyr Gly Ile Ser Asp Tyr
705                 710                 715                 720

Gly Leu Ser Gln Asn Leu Asp Ile Thr Arg Lys Glu Ala Ala Thr Phe
            725                 730                 735

Ile Glu Asn Tyr Leu Asn Ser Phe Pro Gly Val Lys Gly Tyr Met Asp
            740                 745                 750

Asp Ile Val Gln Asp Ala Lys Gln Thr Gly Tyr Val Thr Thr Ile Leu
            755                 760                 765

Asn Arg Arg Arg Tyr Leu Pro Glu Ile Thr Ser Ser Asn Phe Asn Leu
770                 775                 780

Arg Ser Phe Ala Glu Arg Thr Ala Met Asn Thr Pro Ile Gln Gly Ser
785                 790                 795                 800

Ala Ala Asp Ile Ile Lys Lys Ala Met Ile Asp Met Ala Glu Arg Leu
            805                 810                 815

Ile Ser Glu Asn Met Gln Thr Lys Met Leu Leu Gln Val His Asp Glu
            820                 825                 830

Leu Ile Phe Glu Ala Pro Pro Glu Glu Ile Ala Met Leu Glu Lys Ile
            835                 840                 845

Val Pro Glu Val Met Glu Asn Ala Ile Lys Leu Ile Val Pro Leu Lys
850                 855                 860

Val Asp Tyr Ala Phe Gly Ser Ser Trp Tyr Asp Thr Lys
865                 870                 875

<210> SEQ ID NO 4
<211> LENGTH: 2634
<212> TYPE: DNA
<213> ORGANISM: Psychrobacillus sp.

<400> SEQUENCE: 4

```
atgtatttgt caaccgagaa atcctatta ttagacggca atagtttggc ataccgagct     60
ttttttgccc tacctttatt aacaaatgaa catggaatac atacaaacgc agtatatggc    120
tttacaatga tgctacaaaa aattatggat gaagaaaatc ctactcatat gctcgtggca    180
tttgatgccg ggaaaacgac cttccgtcac tctactttg gggattataa aggtggaaga    240
caaaaaacac caccagaact atcggaacaa ttccctttata tacgcaagtt aatcgatgct    300
tatggtatta gcgatacga actggaaatg tacgaagcag acgatattat cggtacttta    360
agcaagcgtg cagacgaaaa agggcagcaa gttgtaattg tctcaggtga taaagattta    420
```

```
acacaactag ctacagataa aacaactgtg tatatcacaa gaaaaggcat aaccgatatt    480
gaaaaatata cacctgaaca tgtacaagaa aagtatggct taactccatt acagattata    540
gacatgaaag gtttaatggg agatgcttct gataatattc caggagttcc tggtgtcgga    600
gaaaaaacag ctattaagct tttaaaagaa catggttcgg tagaggattt atataaagca    660
cttgatacag ttagtggtgt taaactaaag gaaaaactca tcgccaacga agagcaggca    720
attatgagta aggcattagc tacgattgaa acagctgcac cgatacagat ttctatagac    780
gatctttcat atactggtcc taatatggaa gaagtaattg aagtttggaa ggaactagct    840
tttaaaactc ttcttgagaa atctgactat atttctgagg aatccgaaac tacagaagta    900
gcattcgaga ttgttgaaga aattgactct acaatattag ataaagtaat gtcagtccat    960
ttagaaatgt atgatgggca atatcataca agcgaattat taggtattgc tttatcagat   1020
ggagaaaagg gttattttgc tcctgctgat atagcttttc aatcgaagga ttttttgttct   1080 tggttagaaa atgctacgaa taaaaagtat ttagcagact ccaaagcaac acaagcagtg   1140
agtagaaaac ataatgtgaa tgtacatgga gtggaattcg accttctttt agcagcgtat   1200
atagtaaatc ctgctatctc ttcagaggat gttgctgcta ttgctaaaga atttggatat   1260
tttaacttgc tgacaaacga tagtgtttat gggaaaggtg ccaaaaaaac cgcacctgaa   1320
atcgagaaaa ttgcagaaca tgccgtaaga aaagcaaggg ctatttggga cttgaaagaa   1380
aagttagaag taaaactgga agaaaatgaa caatatgcgt tgtataaaga aatagagcta   1440
ccgcttgcat ctatccttgg tacgatggaa tcagatgggg tgctggtgga taaacaaatt   1500
cttgtagaaa tgggtcatga gcttaatatt aagttacgag cgattgaaca agacatttat   1560
gcgttagctg gtgaaacgtt taatattaat tcacctaaac aattaggtgt aatactattt   1620
gaaaaaattg gtcttacccc tattaaaaag acaaaaacgg gctattcaac tgcagcagat   1680
gttttggaaa aactagcaag tgaacatgaa ataatagagc aaatttttact atatcgtcaa   1740 ttaggtaaac tcaattccac atatatcgaa ggattattaa aagagattca tgaagatgat   1800
gggaagatcc atacccgata tcaacaagcc ctaacttcaa ctgggcgttt gagttcgatc   1860
aatccaaacc ttcaaaatat accagttcgt ttagaagaag gtagaaaaat acgtaaagcc   1920
tttgttcctt cacaaccggg atgggtaatg tttgcggcgg attactctca aattgaattg   1980
cgtgttcttg cccatatgtc tgaggatgaa aacctggtag aagcttttaa taatgatctg   2040
gatattcata ctaaaacggc tatggatgta ttccatgtgg agcaggaagc agtaacgtcc   2100
gatatgcgcc gtgctgctaa ggcagttaac tttgggattg tgtatggtat tagtgattat   2160
ggtttatcac aaaacctaga tattactaga aaagaagcgg cgacatttat cgagaattat   2220
ttaaatagct tcccaggtgt aaaaggatat atggatgata tcgttcaaga tgcgaaacaa   2280
acaggctacg ttacaacaat tttgaataga cgaagatatt tgcctgaaat aacaagttct   2340
aactttaatc tccgcagttt tgcagaacgt actgctatga atacaccaat tcaagggagt   2400
gcagccgata ttattaaaaa agcaatgatc gatatggcgg aaagattaat atcagaaaat   2460
atgcagacca aaatgctact acaagtacat gatgaattaa tttttgaggc tccaccagag   2520
gaaattgcaa tgctagaaaa aatagtgcca gaggtgatgg aaaacgctat taaactgatt   2580
gtacctttga aagtggatta tgcctttggt tcatcttggt atgacacgaa gtag           2634
```

<210> SEQ ID NO 5
<211> LENGTH: 297
<212> TYPE: PRT
<213> ORGANISM: Artificial Sequence
<220> FEATURE:
<223> OTHER INFORMATION: Sequence containing a 5'-3' exonuclease functional domain of DNA polymerase I isolated from a Psychrobacillus sp.

<400> SEQUENCE: 5

Met Tyr Leu Ser Thr Glu Lys Ile Leu Leu Asp Gly Asn Ser Leu
1               5                   10                  15

Ala Tyr Arg Ala Phe Phe Ala Leu Pro Leu Leu Thr Asn Glu His Gly
            20                  25                  30

Ile His Thr Asn Ala Val Tyr Gly Phe Thr Met Met Leu Gln Lys Ile
        35                  40                  45

Met Asp Glu Glu Asn Pro Thr His Met Leu Val Ala Phe Asp Ala Gly
    50                  55                  60

Lys Thr Thr Phe Arg His Ser Thr Phe Gly Asp Tyr Lys Gly Gly Arg
65              70                  75                  80

Gln Lys Thr Pro Pro Glu Leu Ser Glu Gln Phe Pro Tyr Ile Arg Lys
            85                  90                  95

Leu Ile Asp Ala Tyr Gly Ile Lys Arg Tyr Glu Leu Glu Met Tyr Glu
        100                 105                 110

Ala Asp Asp Ile Ile Gly Thr Leu Ser Lys Arg Ala Asp Glu Lys Gly
    115                 120                 125

Gln Gln Val Val Ile Val Ser Gly Asp Lys Asp Leu Thr Gln Leu Ala
130                 135                 140

Thr Asp Lys Thr Thr Val Tyr Ile Thr Arg Lys Gly Ile Thr Asp Ile
145                 150                 155                 160

Glu Lys Tyr Thr Pro Glu His Val Gln Glu Lys Tyr Gly Leu Thr Pro
            165                 170                 175

Leu Gln Ile Ile Asp Met Lys Gly Leu Met Gly Asp Ala Ser Asp Asn
        180                 185                 190

Ile Pro Gly Val Pro Gly Val Gly Glu Lys Thr Ala Ile Lys Leu Leu
    195                 200                 205

Lys Glu His Gly Ser Val Glu Asp Leu Tyr Lys Ala Leu Asp Thr Val
210                 215                 220

Ser Gly Val Lys Leu Lys Glu Lys Leu Ile Ala Asn Glu Glu Gln Ala
225                 230                 235                 240

Ile Met Ser Lys Ala Leu Ala Thr Ile Glu Thr Ala Ala Pro Ile Gln
            245                 250                 255

Ile Ser Ile Asp Asp Leu Ser Tyr Thr Gly Pro Asn Met Glu Glu Val
        260                 265                 270

Ile Glu Val Trp Lys Glu Leu Ala Phe Lys Thr Leu Leu Glu Lys Ser
    275                 280                 285

Asp Tyr Ile Ser Glu Glu Ser Glu Thr
290                 295

<210> SEQ ID NO 6
<211> LENGTH: 605
<212> TYPE: PRT
<213> ORGANISM: Artificial Sequence
<220> FEATURE:
<223> OTHER INFORMATION: Truncated DNA polymerase of Aliivibrio salmonicida

```
<400> SEQUENCE: 6

Val Asp Arg Ser Lys Tyr Glu Thr Ile Phe Thr Lys Glu Ala Phe Ser
1               5                   10                  15

Ala Trp Leu Glu Lys Val Asn Asn Ala Glu Val Thr Ala Phe Asp Thr
            20                  25                  30

Glu Thr Asp Ser Leu Asp Tyr Met Val Ala Asn Leu Ile Gly Leu Ser
        35                  40                  45

Phe Ser Val Glu Glu Gly Glu Ala Ala Tyr Val Pro Val Ala His Asp
    50                  55                  60

Tyr Leu Asp Ala Pro Glu Gln Leu Asp Arg Asp Trp Val Leu Ala Gln
65                  70                  75                  80

Leu Lys Pro Tyr Leu Glu Asp Glu Thr Lys Ala Lys Val Gly Gln Asn
                85                  90                  95

Leu Lys Tyr Asp Ala Ser Val Leu Ala Arg Tyr Asp Ile Glu Met Lys
            100                 105                 110

Gly Ile Lys Phe Asp Thr Met Leu Glu Ser Tyr Val Tyr Asn Ser Val
        115                 120                 125

Ala Gly Lys His Asn Met Asp Ser Leu Ala Leu Arg Tyr Leu Gln His
    130                 135                 140

Asn Thr Ile Ser Phe Glu Glu Ile Ala Gly Lys Gly Lys Lys Gln Leu
145                 150                 155                 160

Thr Phe Asn Gln Ile Ala Leu Glu Glu Ala Ala Pro Tyr Ala Ala Glu
                165                 170                 175

Asp Ala Asp Ile Thr Leu Arg Leu His Asn Val Leu His Ala Lys Leu
            180                 185                 190

Val Thr Asp Glu Lys Leu Asn Ala Val Phe Thr Asp Ile Glu Leu Pro
        195                 200                 205

Leu Ile Ser Val Leu Ser Arg Met Glu Arg Lys Gly Val Tyr Ile Asp
    210                 215                 220

Asp Met Leu Leu Ser Ala Gln Ser Leu Glu Ile Gly Gln Arg Leu Asp
225                 230                 235                 240

Glu Leu Glu Thr Ala Ser Phe Glu Val Ala Gly Gln Glu Phe Asn Met
                245                 250                 255

Asn Ser Pro Lys Gln Leu Gln Thr Ile Leu Phe Glu Lys Met Glu Leu
            260                 265                 270

Pro Val Ile Lys Lys Thr Pro Ser Gly Ala Ala Ser Thr Asn Glu Glu
        275                 280                 285

Val Leu Gln Glu Leu Ala Leu Glu Tyr Glu Leu Pro Lys Leu Ile Leu
    290                 295                 300

Glu Tyr Arg Gly Leu Ala Lys Leu Lys Ser Thr Tyr Thr Asp Lys Leu
305                 310                 315                 320

Pro Lys Met Ile Asn Pro Ser Thr Gly Arg Val His Thr Ser Tyr His
                325                 330                 335

Gln Ala Val Thr Ala Thr Gly Arg Leu Ser Ser Thr Asp Pro Asn Leu
            340                 345                 350

Gln Asn Ile Pro Ile Arg Asn Lys Glu Gly Arg Arg Ile Arg Gln Ala
        355                 360                 365

Phe Val Ala Pro His Gly Trp Lys Ile Leu Ala Val Asp Tyr Ser Gln
    370                 375                 380

Ile Glu Leu Arg Ile Met Ala His Leu Ser Gln Asp Arg Ala Leu Leu
385                 390                 395                 400
```

```
Glu Ala Phe Ser Ala Gly Lys Asp Ile His Ala Ala Thr Ala Ala Glu
                405                 410                 415

Val Lys Gly Val Ser Ile Glu Glu Val Thr Ser Glu Asp Arg Arg
        420                 425                 430

Ala Lys Ala Ile Asn Phe Gly Leu Ile Tyr Gly Met Ser Ala Phe Gly
            435                 440                 445

Leu Ala Lys Gln Ile Gly Ile Ser Arg Gly Glu Ala Gln Asp Tyr Met
        450                 455                 460

Asn Val Tyr Phe Glu Arg Tyr Pro Gly Val Met Gln Tyr Met Glu Glu
465                 470                 475                 480

Thr Arg Leu Leu Ala Thr Glu Gln Gly Tyr Val Glu Thr Leu Tyr Gly
                485                 490                 495

Arg Arg Leu Tyr Leu Pro Glu Ile Asn Ala Arg Asn Ala Ile Arg Arg
            500                 505                 510

Lys Ala Ala Glu Arg Ala Ala Ile Asn Ala Pro Met Gln Gly Thr Ala
        515                 520                 525

Ala Asp Ile Ile Lys Lys Ala Met Ile Leu Val Asp Asn Trp Ile Glu
    530                 535                 540

Ala Glu Gly Thr Gly Arg Val Asn Leu Leu Met Gln Val His Asp Glu
545                 550                 555                 560

Leu Val Phe Glu Val Lys Glu Asp Leu Glu Ala Ile Thr Lys Gln
                565                 570                 575

Val Thr Ala Leu Met Glu Ala Ala Val Ser Leu Asp Val Pro Leu Ile
            580                 585                 590

Ala Glu Ser Gly Phe Gly Asp Asn Trp Asp Glu Ala His
        595                 600                 605

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
caccacagaa gtagcattcg agattgtt                                      28

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
ttacttcgtg tcataccaag atgaacc                                       27

<210> SEQ ID NO 9
<211> LENGTH: 82
<212> TYPE: DNA
<213> ORGANISM: Artificial Sequence
<220> FEATURE:
<223> OTHER INFORMATION: molecular beacon template
<220> FEATURE:
<221> NAME/KEY: misc_feature
<222> LOCATION: (7)..(7)
<223> OTHER INFORMATION: labeled with the fluorophore Dabcyl
<220> FEATURE:
<221> NAME/KEY: misc_feature
<222> LOCATION: (32)..(32)
<223> OTHER INFORMATION: labeled with the fluorophore FAM
```

```
<400> SEQUENCE: 9
ggcccgtagg aggaaaggac atcttctagc atacgggccg tcaagttcat ggccagtcaa    60
gtcgtcagaa atttcgcacc ac                                            82

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gtggtgcgaa atttctgac                                                19

<210> SEQ ID NO 11
<211> LENGTH: 19
<212> TYPE: DNA
<213> ORGANISM: Artificial Sequence
<220> FEATURE:
<223> OTHER INFORMATION: Cold primer

<400> SEQUENCE: 11
tatccaccaa tactaccct                                                19

<210> SEQ ID NO 12
<211> LENGTH: 20
<212> TYPE: DNA
<213> ORGANISM: Artificial Sequence
<220> FEATURE:
<223> OTHER INFORMATION: Reporter strand
<220> FEATURE:
<221> NAME/KEY: misc_feature
<222> LOCATION: (20)..(20)
<223> OTHER INFORMATION: labeled with TAMRA fluorophore at 3' end

<400> SEQUENCE: 12
cgatactttg tccactcaat                                               20

<210> SEQ ID NO 13
<211> LENGTH: 40
<212> TYPE: DNA
<213> ORGANISM: Artificial Sequence
<220> FEATURE:
<223> OTHER INFORMATION: Template strand
<220> FEATURE:
<221> NAME/KEY: misc_feature
<222> LOCATION: (1)..(1)
<223> OTHER INFORMATION: labeled at 5' end with the Black Hole Quencher
      2

<400> SEQUENCE: 13
attgagtgga caaagtatcg tagggtagta ttggtggata                         40

<210> SEQ ID NO 14
<211> LENGTH: 40
<212> TYPE: DNA
<213> ORGANISM: Artificial Sequence
<220> FEATURE:
<223> OTHER INFORMATION: Template strand

<400> SEQUENCE: 14
attgagtgga gatagtatcg tagggtagta ttggtggata                         40
```

```
<210> SEQ ID NO 15
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: labeled at 5' end with the fluorophore FAM

<400> SEQUENCE: 15
tatccaccaa tactaccct                                                  19

<210> SEQ ID NO 16
<211> LENGTH: 100
<212> TYPE: DNA
<213> ORGANISM: Artificial Sequence
<220> FEATURE:
<223> OTHER INFORMATION: Template

<400> SEQUENCE: 16
cacaccaaca cacacaacac caacaaccac acaacaccac cacaaccaac acacaacacc     60
gtgtgaattc ggcactggcc gtcgtatgct cttggttgta                          100

<210> SEQ ID NO 17
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: labeled at 5-end with the fluorophore FAM

<400> SEQUENCE: 17
tacaaccaag agcatacgac                                                 20
```